United States Patent
Sankai

(10) Patent No.: US 9,113,797 B2
(45) Date of Patent: Aug. 25, 2015

(54) BLOOD VESSEL CHARACTERISTICS MEASURING APPARATUS AND BLOOD VESSEL CHARACTERISTICS MEASURING METHOD

(75) Inventor: Yoshiyuki Sankai, Ibaraki (JP)

(73) Assignee: University of Tsukuba, Ibaraki (JP)

( * ) Notice: Subject to any disclaimer, the term of this patent is extended or adjusted under 35 U.S.C. 154(b) by 818 days.

(21) Appl. No.: 13/003,017

(22) PCT Filed: Jul. 3, 2009

(86) PCT No.: PCT/JP2009/062217
§ 371 (c)(1),
(2), (4) Date: Jan. 7, 2011

(87) PCT Pub. No.: WO2010/004940
PCT Pub. Date: Jan. 14, 2010

(65) Prior Publication Data
US 2011/0118564 A1    May 19, 2011

(30) Foreign Application Priority Data
Jul. 11, 2008    (JP) .................... 2008-181471

(51) Int. Cl.
*A61B 5/02* (2006.01)
*A61B 5/026* (2006.01)
(Continued)

(52) U.S. Cl.
CPC ........... *A61B 5/0261* (2013.01); *A61B 5/02007* (2013.01); *A61B 5/0285* (2013.01);
(Continued)

(58) Field of Classification Search
CPC ............. A61B 5/02007; A61B 5/0261; A61B 5/0285; A61B 5/02125; A61B 5/0295
USPC ................................................ 600/500–509
See application file for complete search history.

(56) References Cited

U.S. PATENT DOCUMENTS 5,033,472 A * 7/1991 Sato et al. ..................... 600/504
(Continued)

FOREIGN PATENT DOCUMENTS

| JP | 52-052494 | 4/1977 |
| JP | 62-039703 | 3/1990 |

(Continued)

OTHER PUBLICATIONS

Extended European Search Report dated Oct. 1, 2012.

*Primary Examiner* — Navin Natnithithadha
*Assistant Examiner* — Meredith Weare
(74) *Attorney, Agent, or Firm* — IPUSA, PLLC

(57) ABSTRACT

The blood vessel characteristics measuring apparatus 100 includes a blood flow measuring unit 20 held at a position opposed to a skin surface 10 of a measurement region of a subject, an optical sensor unit 30 housed in the blood flow measuring unit 20, an electrocardiograph 40, and a controller 50. The controller 50 includes a blood flow measuring part 60, a blood vessel displacement deriving part 70, and a blood vessel condition deriving part 80. The blood flow measuring part 60 measures the displacements of a blood vessel and tissues around the blood vessel caused by a blood flow based on light intensity at the time of receiving light emitted from a light-emitting part 32 of the sensor unit 30 in light-receiving parts 34 and 36. The blood vessel displacement deriving part 70 derives the wall of the blood vessel 12 based on the displacements of the blood vessel and tissues around the blood vessel. The blood vessel condition deriving part 80 determines pulse wave velocity at each measurement position based on a phase difference between the waveform of the electrocardiographic signal of the electrocardiograph 40 and a detection signal waveform obtained from the light-receiving parts 34 and 36, and derives the condition of the displacement of the wall of the blood vessel 12 from the pulse wave velocity.

12 Claims, 16 Drawing Sheets

(51) Int. Cl.
*A61B 5/0285* (2006.01)
*A61B 5/00* (2006.01)
*A61B 5/021* (2006.01)
*A61B 5/0295* (2006.01)

(52) U.S. Cl.
CPC .............. *A61B 5/417* (2013.01); *A61B 5/6814* (2013.01); *A61B 5/0295* (2013.01); *A61B 5/02125* (2013.01); *A61B 2562/0233* (2013.01); *A61B 2562/046* (2013.01)

(56) References Cited

U.S. PATENT DOCUMENTS

| | | | | |
|---|---|---|---|---|
| 5,513,642 | A * | 5/1996 | Ostrander | 600/334 |
| 5,603,329 | A * | 2/1997 | Hosaka et al. | 600/493 |
| 5,671,750 | A * | 9/1997 | Shinoda | 600/495 |
| 5,853,370 | A * | 12/1998 | Chance et al. | 600/473 |
| 5,995,856 | A * | 11/1999 | Mannheimer et al. | 600/322 |
| 6,280,390 | B1 * | 8/2001 | Akselrod et al. | 600/485 |
| 6,475,153 | B1 | 11/2002 | Khair et al. | |
| 2005/0234317 | A1 * | 10/2005 | Kiani | 600/323 |
| 2007/0213613 | A1 | 9/2007 | Ishida et al. | |
| 2009/0306487 | A1 * | 12/2009 | Crowe et al. | 600/322 |
| 2010/0081940 | A1 | 4/2010 | McKenna | |
| 2010/0234744 | A1 * | 9/2010 | Kawada | 600/500 |

FOREIGN PATENT DOCUMENTS

| | | |
|---|---|---|
| JP | 08-066377 | 3/1996 |
| JP | 08-257002 | 10/1996 |
| JP | 2004-000467 | 1/2004 |
| JP | 2008-048987 | 3/2008 |

* cited by examiner

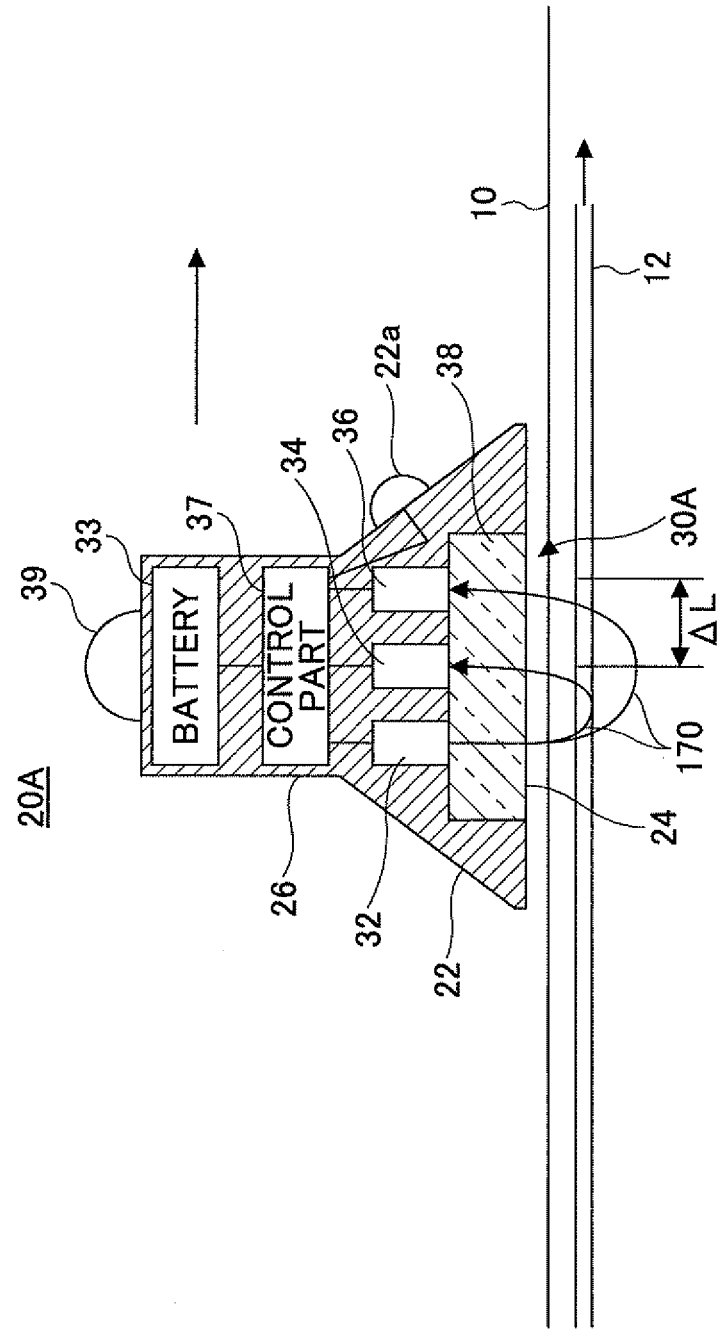

BLOOD VESSEL CHARACTERISTICS MEASURING APPARATUS AND BLOOD VESSEL CHARACTERISTICS MEASURING METHOD

TECHNICAL FIELD

The present invention relates to a blood vessel characteristics measuring apparatus and a blood vessel characteristics measuring method configured to measure, in a contactless manner, a condition inside a blood vessel in which blood flows.

BACKGROUND ART

For example, when blood ejected from the heart is pumped through a blood vessel, the inside diameter of the blood vessel is enlarged by a pressure where a high-pressure region propagates. The development of a pulse wave velocity measuring apparatus is in progress that measures changes inside a blood vessel (artery) by measuring a propagation velocity at which the enlarged portion of the diameter of the blood vessel propagates (also referred to as pulse wave velocity). (See, for example, Patent Document 1.)

According to the pulse wave velocity measuring apparatus, when a time difference is calculated between a periodically occurring predetermined portion of an electrocardiographic lead waveform detected with an electrocardiographic lead unit and a periodically occurring predetermined portion of a pulse wave detected with a pressure pulse wave sensor, the propagation velocity of a pulse wave in an artery is calculated based on the time difference. The propagation velocity is calculated based on a distance including propagation in the aorta connected to the heart. Therefore, in the pulse wave velocity measuring apparatus, the accuracy of the pulse wave velocity increases as the propagation time, that is, the time difference, increases because of a lower pulse wave velocity in the artery due to a long propagation distance and a large aorta diameter.

Further, there is a pulse wave sensor that measures a pulse wave from the waveform of a signal at the time of receiving light that has passed through a blood vessel after exposing a measurement region of a subject to light. (See, for example, Patent Document 2.)

PRIOR ART DOCUMENTS

Patent Document

[Patent Document 1] Japanese Laid-Open Patent Application No. 8-257002
[Patent Document 2] Japanese Laid-Open Patent Application No. 2004-467

SUMMARY OF THE INVENTION

Problems to be Solved by the Invention

However, according to the apparatus described in Patent Document 1 mentioned above, which measures a pulse wave by wrapping a cuff around a part to be subjected to measurement and increasing pressure in the cuff, it is necessary to apply pressure directly to a subject and cause the pulse wave sensor to adhere to the part to be subjected to measurement of the subject. Further, according to the apparatus described in Patent Document 1, the subject is bound during measurement. Therefore, in the case of performing measurement at multiple points on the same subject, the subject has to be bound for a long period of time, thus causing the problem of an increased burden on the subject.

Further, according to the pulse wave sensor described in Patent Document 2 mentioned above, which exposes a fingertip to light and measures a blood flow from the detection signal of light, in the case of pressing the fingertip hard, the skin of the fingertip comes into contact with a light receiving part, so that the fingertip is pressed, thus causing a problem in that a blood flow in a blood vessel of the fingertip varies to reduce the accuracy of measurement.

Accordingly, in view of the above, the present invention has an object of reducing the above-mentioned burden on a subject and solving reduction in the accuracy of measurement.

Means for Solving the Problems

In order to solve the above-described problems, the present invention includes such means as follows.

(1) The present invention solves the above-described problems by including a sensor unit provided at a position opposed to a measurement region of a subject, the sensor unit including a light-emitting part configured to emit light onto the measurement region and a light-receiving part configured to contactlessly receive the light propagated through the measurement region; a blood flow measuring part configured to measure a displacement of a blood vessel and a displacement of a tissue around the blood vessel caused by a blood flow in the measurement region based on a light intensity at a time of receiving the light emitted from the light-emitting part in the light-receiving part; a blood vessel displacement deriving part configured to derive a displacement of a wall of the blood vessel based on the displacement of the blood vessel and the displacement of the tissue around the blood vessel obtained by the blood flow measuring part; an electrocardiographic measurement part configured to measure an electrocardiographic signal of the subject; and a blood vessel condition deriving part configured to derive a condition of the wall of the blood vessel at each of measurement positions based on a difference between a waveform of the electrocardiographic signal and a detection signal waveform obtained from the light-receiving part.

(2) The present invention solves the above-described problems by the blood vessel condition deriving part being configured to derive the condition of the wall of the blood vessel at each of the measurement positions based on a phase difference between the waveform of the electrocardiographic signal and the detection signal waveform obtained from the light-receiving part in the blood vessel characteristics measuring apparatus described in (1).

(3) The present invention solves the above-described problems by optically measuring a blood cell component according to the condition of the wall of the blood vessel in the blood vessel characteristics measuring apparatus described in (1).

(4) The present invention solves the above-described problems by the sensor unit including plural of the light-emitting parts configured to emit light onto a plurality of measuring points of the subject and plural of the light-receiving parts configured to contactlessly receive the light propagated through the measuring points, and the blood vessel condition deriving part being configured to derive the condition of the wall of the blood vessel at each of the measurement positions based on differences between the waveform of the electrocardiographic signal and the detection signal waveform obtained from the light-receiving parts in the blood vessel characteristics measuring apparatus described in (1).

(5) The present invention solves the above-described problems by the light-receiving parts including a first light-receiving part configured to measure a propagation intensity of the light over an upstream portion of the blood vessel in the measurement region; and a second light-receiving part provided on a downstream side of the first light-receiving part over the blood vessel and configured to measure the propagation intensity of the light over a downstream portion of the blood vessel in the measurement region in the blood vessel characteristics measuring apparatus described in (4).

(6) The present invention solves the above-described problems by the light-receiving parts being circumferentially arranged at predetermined intervals at different radial positions around the light-emitting part in the blood vessel characteristics measuring apparatus described in (4).

(7) The present invention solves the above-described problems by the sensor unit being provided in a movable blood vessel measuring unit and being configured to measure a propagation intensity of the light in any measurement region in the blood vessel characteristics measuring apparatus described in (1).

(8) The present invention solves the above-described problems by the blood flow measuring unit including a battery configured to supply the sensor unit with an electric current; and a radio communications unit configured to transmit a detection signal detected in the sensor unit by radio in the blood vessel characteristics measuring apparatus described in (7).

(9) The present invention solves the above-described problems by plural of the sensor units being supported at a plurality of points of a netted base configured to be attached to a head of the subject and being configured to measure a propagation intensity of the light at the respective measurement positions of the head of the subject in the blood vessel characteristics measuring apparatus described in (1).

(10) The present invention solves the above-described problems by the light-receiving parts being arranged at predetermined intervals so as to be opposed from outside to a surface of the head, and the blood vessel condition deriving part being configured to derive the condition of the blood vessel at each of the measurement positions of the head based on differences between the waveform of the electrocardiographic signal and detection signal waveforms obtained from the light-receiving parts in the blood vessel characteristics measuring apparatus described in (9).

(11) The present invention solves the above-described problems by the blood flow measuring part being configured to map measurement data obtained from the light-emitting parts based on addresses relative to the head, and to store the displacement of the blood vessel in a database with respect to each of the measurement positions corresponding to the addresses, and the blood vessel condition deriving part being configured to generate an image of blood vessel characteristics of the entire head by deriving the condition of the blood vessel at each of the measurement positions of the head by reading the displacement of the blood vessel at each of the measurement positions from the database and extracting the displacement of the blood vessel corresponding to each of the addresses in the blood vessel characteristics measuring apparatus described in (9).

(12) The present invention solves the above-described problems by causing a light-emitting part of a sensor unit provided to be opposed to a measurement region of a subject to emit light onto the measurement region and receiving the light propagated through the measurement region in a light-receiving part of the sensor; measuring a displacement of a blood vessel and a displacement of a tissue around the blood vessel caused by a blood flow in the measurement region based on a detection signal of a light intensity at a time of receiving the light emitted from the light-emitting part in the light-receiving part; deriving a displacement of a wall of the blood vessel based on the displacement of the blood vessel and the displacement of the tissue around the blood vessel; measuring an electrocardiographic signal of the subject; and deriving a condition of the wall of the blood vessel at each of measurement positions based on a difference between a waveform of the electrocardiographic signal and a detection signal waveform obtained from the light-receiving part.

Effects of the Invention

According to the present invention, the condition of the wall of a blood vessel at each measurement position is derived based on a difference between the waveform of a light-receiving part configured to contactlessly receive light propagated through a measurement region and the waveform, of an electrocardiographic signal. Therefore, it is possible to measure the condition of the blood vessel without contact with a subject, and there is no binding of the subject. Accordingly, it is possible to reduce a burden on the subject. Further, according to the present invention, the condition of the blood vessel is measured without pressing the blood vessel. Therefore, the accuracy of measurement is high, so that it is possible to measure blood vessel characteristics data according to the condition of the wall of the blood vessel even in a head having a large number of blood vessels, for example.

BRIEF DESCRIPTION OF THE DRAWINGS

FIG. 6 is a longitudinal cross-sectional view illustrating a first variation of a blood flow measuring part.

MODES FOR CARRYING OUT THE INVENTION

For a more detailed description of the present invention, a description is given below, with reference to the drawings, of embodiments of the present invention.

First Embodiment

Figure 1:
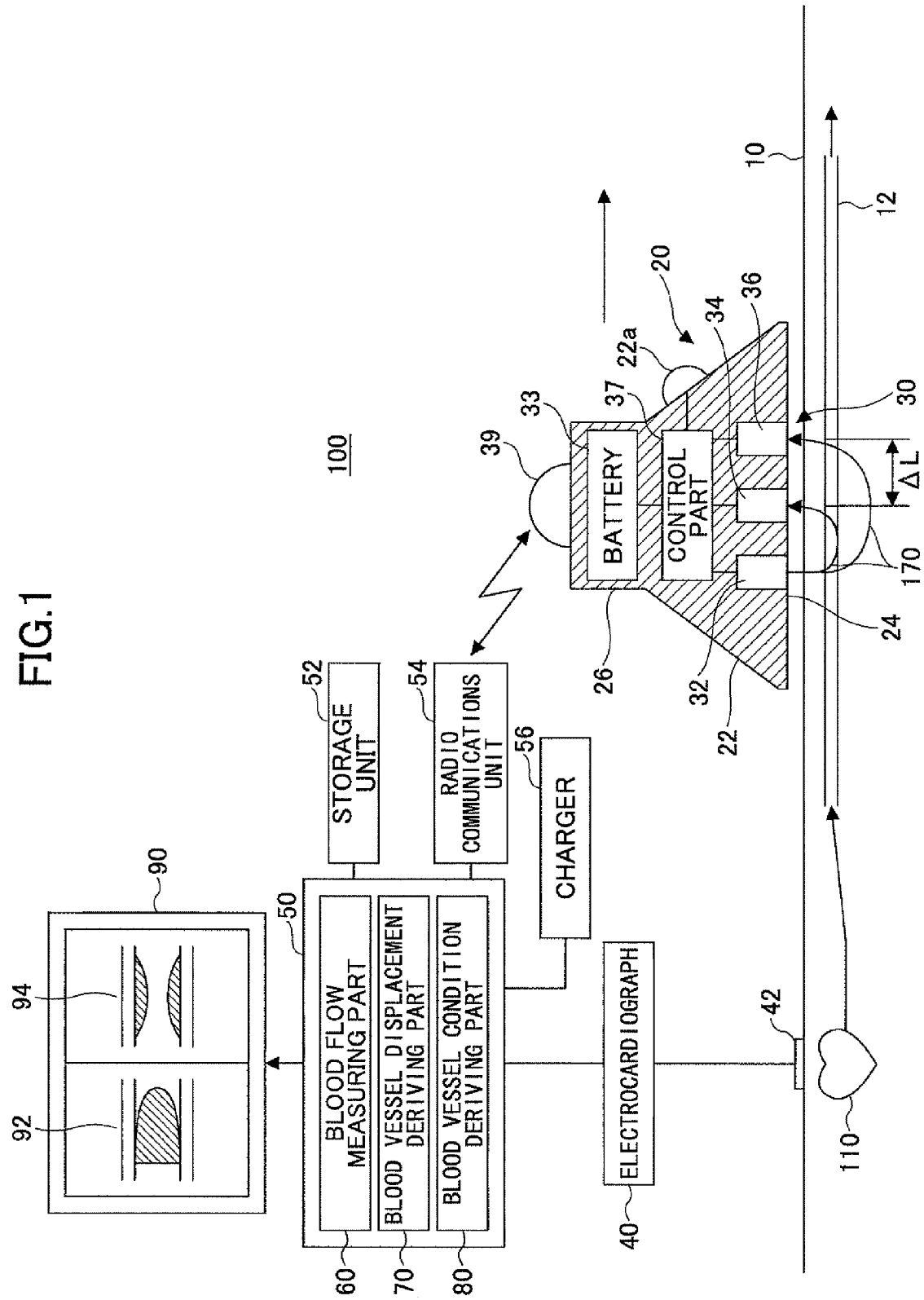
FIG. 1 is a system diagram illustrating a general configuration of a first embodiment of a blood vessel characteristics measuring apparatus according to the present invention.

FIG. 1 is a system diagram illustrating a general configuration of a first embodiment of a blood vessel characteristics measuring apparatus according to the present invention. As illustrated in FIG. 1, a blood vessel characteristics measuring apparatus 100 includes a mobile blood flow measuring unit 20, an optical sensor unit 30, an electrocardiograph (an electrocardiographic measurement part) 40, and a controller 50. The blood flow measuring unit 20 measures a blood flow at a position opposed to a skin surface 10 of a measurement region of a subject. The sensor unit 30 includes an optical sensor housed in the blood flow measuring unit 20 and configured to measure a blood flow running through a blood vessel in a contactless manner. The electrocardiograph (electrocardiographic measurement part) 40 measures cardiac potential and outputs a cardiac potential signal. The controller 50 derives the characteristics of the blood vessel (the modulus of elasticity of the blood vessel, the amount of plaque inside the blood vessel, and the degree of arteriosclerosis) based on the difference between the detection signals of the sensor unit 30 and the cardiac potential signal of the electrocardiograph 40.

The blood flow measuring unit 20 is formed to be a portable size. For example, the blood flow measuring unit 20 may be suitably moved depending on in which part of a human body a blood flow is to be measured, so as to allow measurement of a blood flow in any measurement region. Further, according to the blood flow measuring unit 20, the base of a conical part 22 is a measurement surface 24 to be opposed (in proximity without contact) to the measurement region, and a holding part 26 is projecting on top of the conical part 22. Accordingly, a measurer who measures blood vessel characteristics may contactlessly measure the displacements of the blood vessel and the tissues around the blood vessel due to the blood flow of the measurement region by holding the holding part 26 and suitably opposing the measurement surface 24 on the base side to the skin surface 10 of the measurement region.

The sensor unit 30 includes a light-emitting part 32 and a pair of light-receiving parts 34 and 36. The light-emitting part 32 is a light source to emit laser light onto the subject. Each of the paired light-receiving parts 34 and 36 is provided on the downstream side of the light emission point of the light-emitting part 32, and outputs a signal according to the intensity of received light.

Further, the blood flow measuring unit 20 includes a rechargeable battery 33, a control part 37, and a radio communications unit 39. The control part 37 supplies the light-emitting part 32 with electric current from the battery 33 to cause the light-emitting part 32 to emit light, and reads received light signals from the light-receiving parts 34 and 36 that have received light propagated on or through the skin surface 10. The radio communications unit 39 performs radio communications with the controller 50, and transmits the received light signals from the light-receiving parts 34 and 36 to the controller 50 by radio.

Further, a pilot light 22a for indicating being on the downstream side (the light-receiving parts 34 and 36 side) of the light-emitting part 32 is provided at a downstream inclined position on the conical part 22. The pilot light 22a is a moving direction indicator light formed of, for example, a light-emitting diode and indicating a light-receiving direction (moving direction) by flashing in a certain period. Further, the pilot light 22a also serves as a warning light for preventing loss due to wirelessness and as a charging indicator light that indicates charging by switching from flashing to continuous lighting when it becomes necessary to charge the battery 33.

The blood flow measuring unit 20, which is a wireless unit capable of performing short-range communications with the controller 50 using weak radio waves, may be freely moved to a measurement area. Further, the rechargeable battery 33 of the blood flow measuring unit 20 is suitably charged at a non-use time when no blood flow measurement is being performed.

The light-emitting part 32 and the paired light-receiving parts 34 and 36 have their respective light-emitting surface and light-receiving surfaces provided in the same plane as the measurement surface 24 formed on the lower surface of the sensor unit 30. Therefore, when the skin surface 10 of any measurement region is exposed to laser light A from the light-emitting part 32, the laser light A is transmitted through a blood flow running through a blood vessel 12 below the skin surface 10 as well as reflected from the skin surface 10 to propagate to the measurement surface 24.

Each of the paired light-receiving parts 34 and 36 receives light radiated from the skin surface 10 (light including reflected light and transmitted light), and outputs an electrical signal corresponding to the amount of light received (light intensity). Then, the control part 37 of the blood flow measuring unit 20 causes the detection signals detected by the light-receiving parts 34 and 36 to be converted into radio signals and transmitted to the controller 50 by the radio communications unit 39. The detection signals from the light-receiving parts 34 and 36 are output as signals of a predetermined period or continuous signals based on a light-emitting signal from the light-emitting part 32.

Further, the radio communications unit 39, which is provided at the upper end of the holding part 26 so as to facilitate transmission of a detection signal of the blood flow measuring unit 20, is protected by a hemispherical protective cover.

The electrocardiograph 40 measures a cardiac potential generated in accordance with the motion of a heart 110 with electrodes 42 adhering to the skin of the subject. The electrodes 42 may be attached to any places near the heart 110 where it is easy to detect a cardiac potential. In the case of performing a common electrocardiogram measurement, electrodes are attached to four locations of the limbs for limb leads and six locations of the chest for chest leads. In the present invention, however, since it is not that the motion of the heart 110 is observed from an electrocardiogram but that blood vessel characteristics are measured using the waveform of a cardiac potential as a trigger, the cardiac potential may be measured at one location.

The controller 50, which is composed of a personal computer, etc., includes a blood flow measuring part 60, a blood vessel displacement deriving part 70, and a blood vessel condition deriving part 80 that read various control programs contained in a storage unit 52 and execute various control processes. The blood flow measuring part 60 measures the displacements of the blood vessel 12 and tissues around the blood vessel 12 due to a blood flow based on light intensity at the time of the light-receiving parts 34 and 36 receiving light emitted from the light-emitting part 32 of the sensor unit 30. The blood vessel displacement deriving part 70 derives the displacement of the wall of the blood vessel 12 based on the displacements of the blood vessel 12 and tissues around the blood vessel 12. The blood vessel condition deriving part 80 determines a pulse wave velocity at each measurement position based on a phase difference between the waveform of the electrocardiographic signal of the electrocardiograph 40 and a detection signal waveform obtained from the light-receiving parts 34 and 36, and derives the condition of the wall of the blood vessel 12 from the pulse wave velocity.

Further, the controller 50 includes the storage unit 52, a radio communications unit 54, and a charger 56. The storage unit 52 constitutes a database configured to store the above-mentioned control programs and the measurement data and operational results transmitted from the blood flow measuring unit 20. The radio communications unit 54 performs data communications with the radio communications unit 39 of the blood flow measuring unit 20 by radio. The charger 56 allows attachment of the blood flow measuring unit 20 to charge the battery 33 of the blood flow measuring unit 20 when no measurement is being performed.

The controller 50, in response to reception of measurement data transmitted from the blood flow measuring unit 20 in the radio communications unit 54, automatically stores the measurement data in the database of the storage unit 52. In the database, the wall displacement data of a blood vessel (the contraction of the inside diameter of a blood vessel) corresponding to the measurement results of the displacements of a blood vessel and tissues around the blood vessel due to a blood flow and blood vessel characteristics data corresponding to a phase difference T between the cardiac potential signal waveform of the electrocardiograph 40 and the detection signal waveform of the light-receiving parts 34 and 36 are prestored. The blood vessel characteristics include the modulus of elasticity of a blood vessel, the amount of plaque inside a blood vessel (the buildup of a tunica intima), and the degree of arteriosclerosis.

The controller 50 is connected to a monitor 90. The controller 50 generates image data from the measurement data of a blood flow measured with the sensor unit 30 of the blood flow measuring unit 20, and causes a blood flow measurement image 92 and a blood vessel characteristic result image 94 based on the image data to be displayed on the monitor 90.

This allows a measurer to determine whether the blood flow is normal by moving close and placing the measurement surface 24 to oppose the skin surface 10 of the subject (without contact) while holding the blood flow measuring unit 20 in her/his hand, watching the measurement image 92 and the blood vessel characteristic result image 94 displayed on the monitor 90.

Thus, according to the blood vessel characteristic measuring apparatus 100, the blood flow measuring unit 20 may be moved to any measurement region, so that it is possible to measure blood vessel characteristics in any part of the subject. Further, since the blood flow measurement part 20 is a noncontact type, it is possible to perform a measurement operation easily without binding the subject, and to measure blood vessel characteristics efficiently in a short period of time without the necessity of attachment and detachment operations unlike a method in which there is contact with a subject.

Here, a description is given of the principle of a blood flow measuring method.

Figure 2:
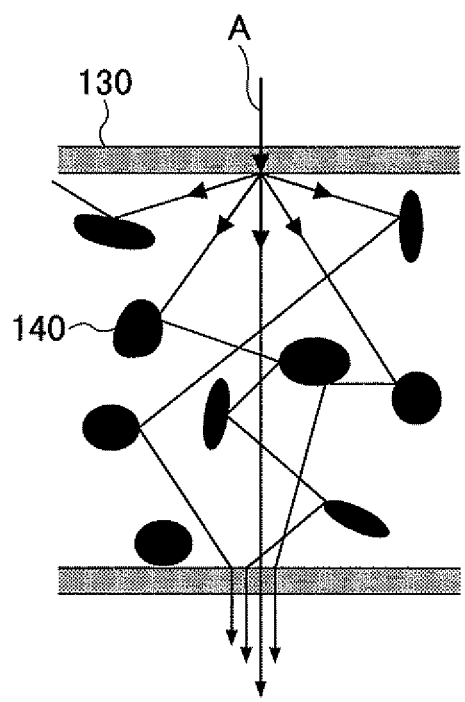
FIG. 2 is a diagram for illustrating the principle of a blood flow measuring method.

FIG. 2 is a diagram for illustrating the principle of a blood flow measuring method. As illustrated in FIG. 2, when blood is exposed to the external laser light A, the laser light A that has entered a blood layer 130 is transmitted and travels through the blood as light of both a reflected and scattered light component due to normal erythrocytes 140 and a reflected and scattered light component due to adhering thrombi.

The effects exerted on light during its transmission through the blood layer 130 vary every moment depending on the blood condition. Therefore, it is possible to observe various changes in the blood condition by continuously measuring the amount of transmitted light (alternatively, the amount of reflected light) and observing a change in the light amount.

In the case of measuring the blood vessel characteristics of the subject using the above-described blood flow measuring unit 20, when the measurement surface 24 of the blood flow measuring unit 20 is moved close and opposed to the skin surface 10, which is a subject of measurement, the blood vessel 12 and its surrounding tissues of the opposite skin surface 10 deform between the light-emitting part 32 and the light-receiving parts 34 and 36 of the sensor unit 30, so that the condition of the amount of transmission of light or the amount of reflection of light changes to cause variations in the detection signals of the light-receiving parts 34 and 36.

Accordingly, in the blood flow measuring unit 20, light is emitted from the light-emitting part 32 onto the skin surface 10, so that of the light received by the light-emitting parts 34 and 36, some components are transmitted through the skin to reach the blood vessel 12 and travel through blood to be received by the light-receiving parts 34 and 36 while other components are reflected from the skin surface 10 to be received by the light-emitting parts 34 and 36. That is, since the component of light reflected from the skin surface 10 to be received is greater than the amount of light transmitted through the blood vessel 12, the displacement of tissues around the blood vessel displaced with the pulsation of the blood vessel 12 may be measured with light reflected from the skin surface 10.

Here, a change in hematocrit (Hct: the volume ratio of erythrocytes per unit volume, that is, the volume concentration of erythrocytes per unit volume) or the like is also a factor related to a change in hemoglobin concentration and affects a change in the amount of light. The basic principle in this embodiment is that the condition of a blood flow is measured by changes in a light path and the amount of transmitted light caused by the blood flow using the laser light A as described above and the condition of brain activity is further measured from the condition of a blood flow inside the brain.

Further, a description is given, with a principle configuration, of features of the present invention. The optical characteristics of blood are determined by blood cell components (hemoglobin inside erythrocyte cells in particular). Further, since hemoglobin has a disposition to easily bind oxygen, erythrocytes also serve to carry oxygen to brain cells. The oxygen saturation of blood is a numerical value that represents the percentage of hemoglobin binding oxygen in blood. Further, the oxygen saturation, which is correlated with the partial pressure of oxygen ($PaO_2$) in arterial blood, is an important index of the respirator function (gas exchange).

It is known that the oxygen saturation is high if the partial pressure of oxygen is high. If the oxygen saturation varies, the amount of light transmitted through blood also varies. Therefore, in measuring a blood flow, the measurement may be performed with more accuracy by eliminating the effect of the oxygen saturation.

Further, factors affecting the partial pressure of oxygen ($PaO_2$) include alveolar ventilation, environments such as atmospheric pressure and the fraction of inspired oxygen ($FiO_2$), and alveolar gas exchanges such as the ventilation-perfusion ratio, the gas diffusion capacity, and the shunt rate.

The controller 50 includes an operation part that performs signal processing according to the amount of light (the intensity of light) received by the light-receiving parts 34 and 36 of the sensor unit 30. As described below, the operation part performs an operation for detecting the conditions of the displacements of a blood vessel and tissues around the blood vessel caused by a blood flow based on measured values output from the light-receiving parts 34 and 36 of the sensor unit 30.

The laser light A of the light-emitting part 32 is emitted as pulsed light emitted intermittently at predetermined time intervals (for example, 10 Hz through 1 MHz) or continuous light. In the case of thus using pulsed light, a flash frequency, or a frequency at which the pulsed light flashes, is determined in accordance with the blood flow velocity, and the measurement is performed continuously or at a measurement sampling frequency two or more times the flash frequency. Further, in the case of using continuous light, the measurement sampling frequency is determined in accordance with the blood flow velocity, and the measurement is then performed.

Through respiration, the hemoglobin (Hb) in blood chemically reacts with oxygen to form $HbO_2$ in a lung, thereby bringing oxygen into blood. The degree of bringing oxygen into blood (oxygen saturation) slightly differs depending on the condition of respiration, etc. That is, in the present invention, based on the discovery of the phenomenon that the light absorption coefficient varies depending on the oxygen saturation when blood is exposed to light, it is determined that the effect of the oxygen saturation should be eliminated because this phenomenon becomes an element of disturbance in the measurement of a blood flow with the laser light A.

Figure 3:
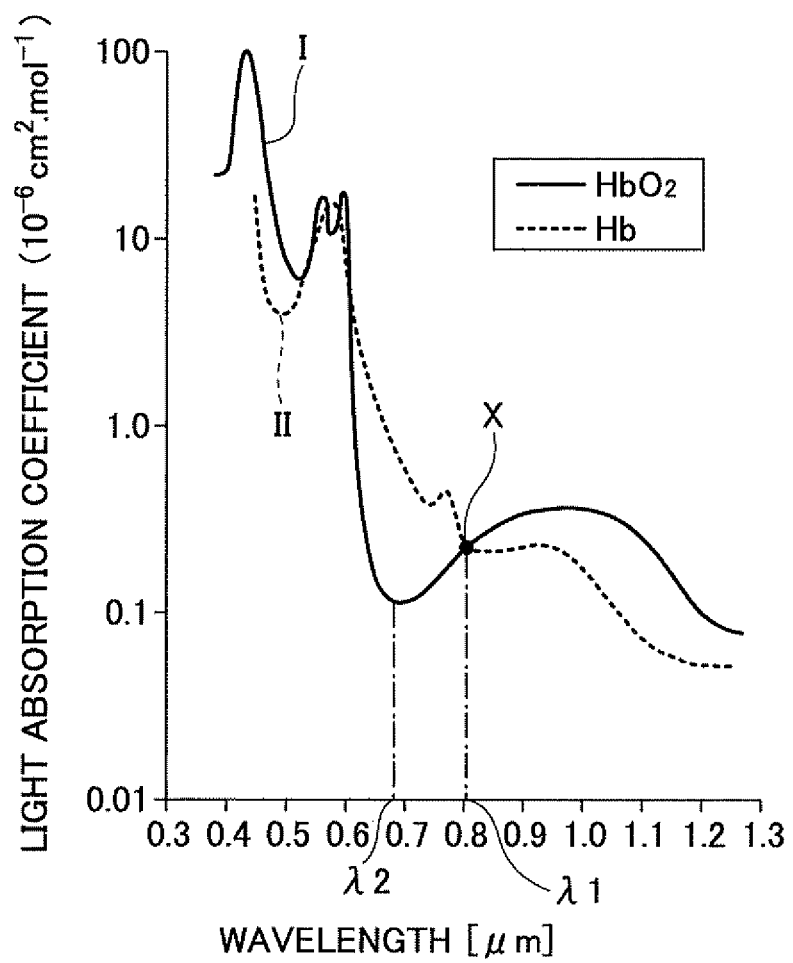
FIG. 3 is a graph illustrating the relationship between the wavelength of laser light and the light absorption condition with different oxygen saturations of blood.

FIG. 3 is a graph illustrating the relationship between the wavelength of laser light and the light absorption condition with different oxygen saturations of blood. In the body, the hemoglobin contained in erythrocytes is divided into oxyhemoglobin, or hemoglobin binding oxygen, ($HbO_2$: Graph II, indicated by broken line) and non-oxidized hemoglobin (Hb: Graph I, indicated by solid line). The light absorption coefficient differs greatly between the conditions illustrated in the two graphs. For example, oxygen-rich blood has a vivid color as fresh blood. On the other hand, venous blood, from which oxygen is released, is dull-colored and dark. As illustrated in Graphs I and II of FIG. 3, these conditions of the light absorption coefficient vary in a wide wavelength region of light.

It is shown that by selecting a particular wavelength from Graphs I and II of FIG. 3, it is possible to expose blood to light and measure a blood flow without any effect on the light absorption coefficient even if the oxygen saturation of hemoglobin in erythrocytes varies greatly because of intravital oxygen metabolism, etc.

The light absorption coefficient is low in a certain wavelength region independent of the oxygen saturation of hemoglobin in erythrocytes. Based on this, it is determined whether light is easily transmitted through a blood layer with a wavelength $\lambda$. Accordingly, by using light in a predetermined wavelength region (for example, $\lambda$ of around 800 nm to around 1300 nm), it is possible to measure a blood flow with a reduced effect of oxygen saturation.

Therefore, a wavelength region of approximately 600 nm to approximately 1500 nm is employed for the laser light A used in the present invention. As a result, the light absorption coefficient of hemoglobin (Hb) is sufficiently low for practical use, and the region includes an isosbestic point X. Therefore, measuring points of two or more wavelengths are used, and may be regarded as an isosbestic point in terms of calculation. That is, it is possible to have specifications that are not affected by oxygen saturation. With respect to other wavelength regions, the light absorption coefficient is increased and the S/N is lowered if $\lambda$ is less than 600 nm, and with a wavelength $\lambda$ of 1500 nm or higher, the light-receiving sensitivity of the light-receiving parts 34 and 36 is insufficient so that the measurement is affected by disturbances such as other blood components, thus being prevented from having accuracy.

Therefore, according to this embodiment, a light-emitting element formed of a wavelength turnable semiconductor laser is used for the light-emitting part 32, and the laser light A emitted from the light-emitting part 32 is set to two kinds of wavelengths, that is, $\lambda 1=805$ nm, at which Graphs I and II have the isosbestic point X (first light), and $\lambda 2=680$ nm, where the light absorption coefficient is lowest in Graph I (second light).

Here, a description is given of a method of detecting erythrocyte concentrations R, Rp, and Rpw based on the amount of transmitted light in the case of receiving the laser light A propagated through a light propagation path.

Computing Equation (1) of the erythrocyte concentration R in the case of using a one-point-one-wavelength technique employed in the conventional measurement method may be expressed as the following equation:

$$R=\log_{10}(Iin/Iout)=f(Iin,L,Ht). \quad (1)$$

According to the method of Eq. (1), the erythrocyte concentration is a function of the amount of entered and transmitted light Iin of the laser light A transmitted from the light-emitting part 32, a distance (light path length) between the light-emitting part 32 and the light-receiving part 34 or 36, and the above-described hematocrit (Ht). Therefore, in the case of determining the erythrocyte concentration according to the method of Eq. (1), it is difficult to measure the erythrocyte concentration with accuracy because the erythrocyte concentration varies depending on the three factors.

Computing Equation (2) of the erythrocyte concentration Rp in the case of using a two-point-one-wavelength technique according to this embodiment may be expressed as the following equation:

$$Rp=\log_{10}\{Iout/(Iout-\Delta Iout)\}=\Phi(\Delta L,Ht). \quad (2)$$

According to the method of Eq. (2), light is received at two points (the light-receiving parts 34 and 36 of the sensor unit 30) at different distances from the laser light A as illustrated in FIG. 1, so that the erythrocyte concentration is a function of a distance $\Delta L$ between the two light-receiving parts 34 and 36 and the above-described hematocrit (Ht). Therefore, in the case of determining the erythrocyte concentration according to the method of Eq. (2), since the distance $\Delta L$ between the light-receiving parts 34 and 36 is preknown among the two factors, the erythrocyte concentration is measured as a value having the hematocrit (Ht) as a coefficient. Accordingly, this computing method allows the erythrocyte concentration to be measured with accuracy as a measurement according to the hematocrit (Ht).

Further, Computing Equation (3) of the erythrocyte concentration Rpw in the case of a two-point-two-wavelength technique according to a variation of this embodiment may be expressed as the following equation:

$$Rpw=[\log_{10}\{Iout/(Iout-\Delta Iout)\}\lambda 1]/[\log_{10}\{Iout/(Iout-\Delta Iout)\}\lambda 2]=\zeta(Ht). \quad (3)$$

According to the method of Eq. (3), the wavelength of the laser light A emitted from the light-emitting part 32 is set to different λ1 and λ2 (λ1=805 nm and λ2=680 nm in this embodiment), so that the erythrocyte concentration is measured as a function of only the hematocrit (Ht). Therefore, according to this computing method, it is possible to measure the erythrocyte concentration with accuracy as a measurement according to the hematocrit (Ht). In this embodiment, the erythrocyte concentration Rp of erythrocytes flowing through a blood vessel is measured according to the measurement method of the two-point-one-wavelength technique using Eq. (2) described above.

That is, the erythrocyte concentration is a function of the distance ΔL between the light-receiving parts 34 and 36 and the above-described hematocrit (Ht). Therefore, when determining the erythrocyte concentration Rp, the erythrocyte concentration is measured as a value having the hematocrit (Ht) as a coefficient because the distance ΔL between the light-receiving parts 34 and 36 is preknown among the two factors. Therefore, according to this computing method, it is possible to measure the erythrocyte concentration with accuracy as a measurement according to the hematocrit (Ht), so that it is possible to measure the condition of a blood flow with accuracy. Thus, the condition of a blood flow may be measured without being affected by disturbing light or the like. Therefore, there is no need to cause the sensor unit to adhere to the surface of a measurement region.

Figure 4:
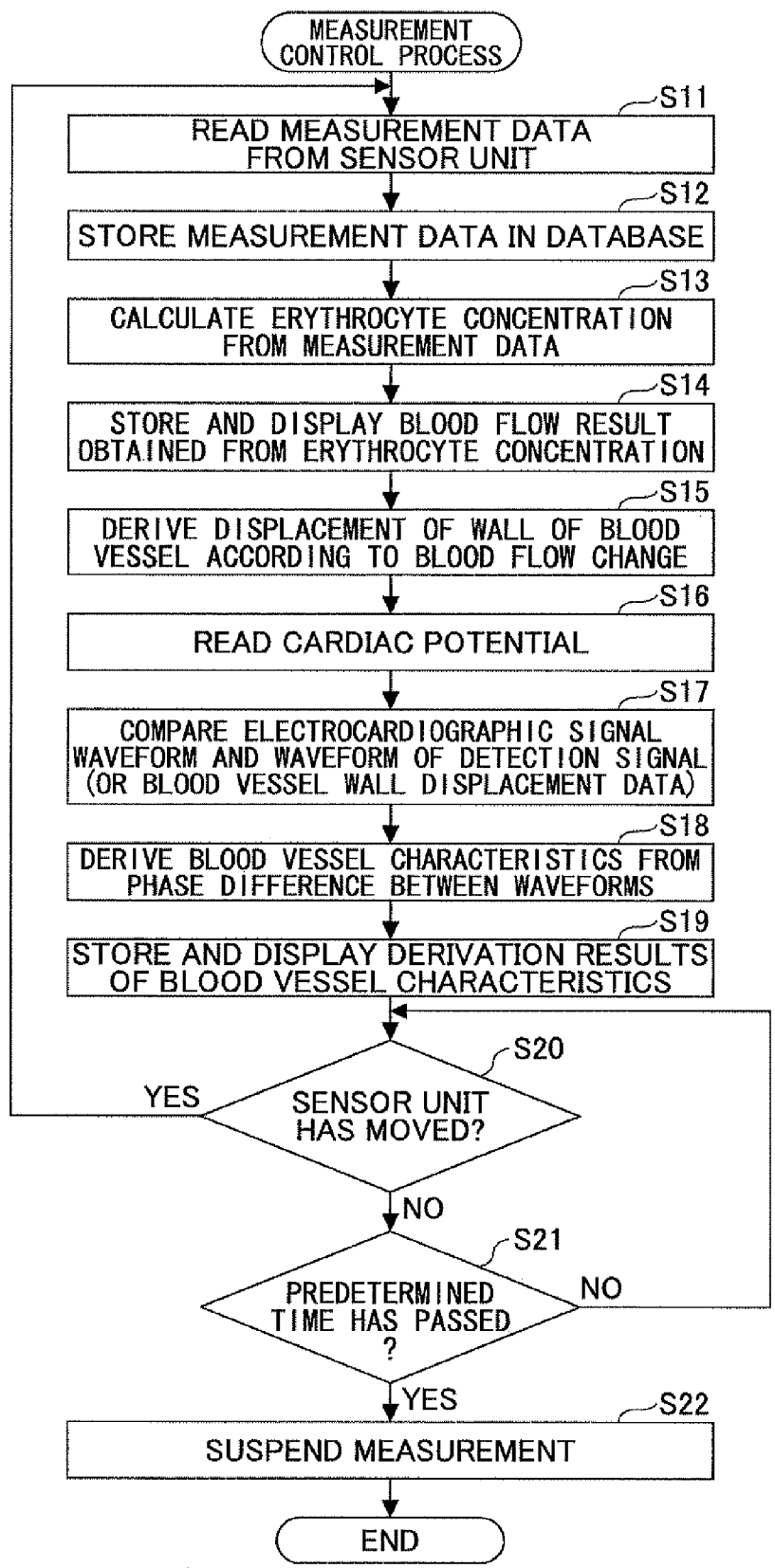
FIG. 4 is a flowchart illustrating a measurement control process executed by a controller.

Here, a description is given, with reference to the flowchart of FIG. 4, of a measurement control process executed by the controller 50. In S11 of FIG. 4, when the measurement data (detection signals) detected in the light-receiving parts 34 and 36 of the sensor unit 30 are received in the radio communications unit 54, the measurement data are read.

Next, in S12, the read measurement data are stored in the database of the storage unit 52.

Next, in S13, the erythrocyte concentration Rp of erythrocytes flowing through the blood vessel 12 is computed according to the measurement method of the two-point-one-wavelength technique using Eq. (2) described above. Then, in S14, a blood flow change in a measurement region obtained based on the erythrocyte concentration Rp is stored in the database of the storage unit 52, and the blood flow measurement image 92 corresponding to the conditions of the displacements of the blood vessel 12 and tissues around the blood vessel 12 caused by the blood flow of this time is displayed on the monitor 90.

Next, in S15, the wall displacement data of a blood vessel (the contraction of the inside diameter of a blood vessel) corresponding to the conditions of the displacements of the blood vessel 12 and tissues around the blood vessel 12 caused by the blood flow are derived from the database.

Next, in S16, a signal of cardiac potential detected by the electrocardiograph 40 is read. Then, in S17, the cardiac potential signal waveform of the electrocardiograph 40 and the detection signal waveform of the light-receiving parts 34 and 36 (or the waveform of the wall displacement data corresponding to the blood flow change) are compared.

Figure 5:
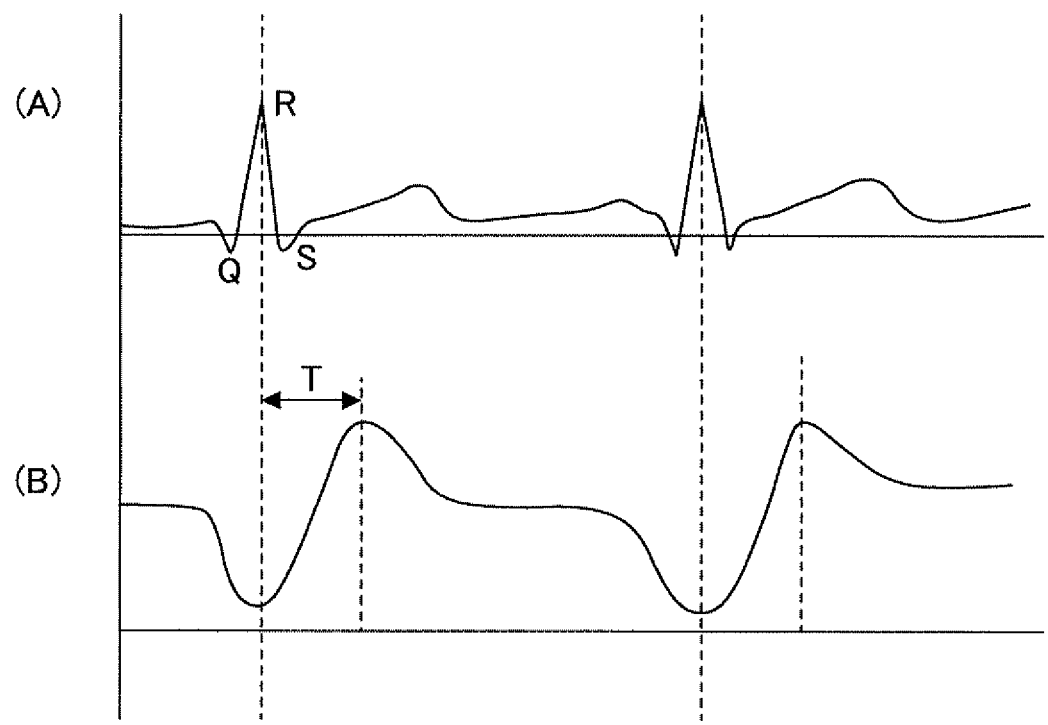
FIG. 5 is a diagram comparing a cardiac potential signal waveform (A) and a light-receiving part detection signal waveform (B).

FIG. 5 is a diagram comparing a cardiac potential signal waveform (A) and a light-receiving part detection signal waveform (B). In S17, as illustrated in FIG. 5, a phase difference T between a point corresponding to the peak value of the R wave among the Q wave, R wave, and S wave of the cardiac potential signal waveform (A) and a point indicating the highest value of the light-receiving part detection signal waveform (B) is determined.

In S18, the pulse wave velocity is determined by dividing the distance between the heart 110 and the measurement region by the phase difference T between the cardiac potential signal waveform of the electrocardiograph 40 and the detection signal waveform of the light-receiving parts 34 and 36. Further, the blood vessel characteristics (the modulus of elasticity of the blood vessel, the amount of plaque inside the blood vessel, and the degree of arteriosclerosis) of the measurement region corresponding to the pulse wave velocity are derived from the database, thereby deriving the degree of arteriosclerosis of the blood vessel 12 in the measurement region. Next, in S19, the degree of arteriosclerosis, which is the result of the derivation of the blood vessel characteristics, is stored in the database of the storage unit 52, and the blood vessel characteristic result image 94 corresponding to the degree of arteriosclerosis obtained this time is displayed on the monitor 90.

Next, in S20, it is determined whether the sensor unit 30 has moved. In S20, if there is a variation in the detection signal waveform of the light-receiving parts 34 and 36, it is determined that the sensor unit 30 has moved from a position opposed to the measurement region, and the process returns to S11 to repeat the control process of S11 through S20. In S20, for example, if the measurement surface 24 is a predetermined distance or more apart from the skin surface 10 so that the light-receiving parts 34 and 36 are unable to receive light from the light-emitting part 32, thus reducing the level of the detection signals to zero, it is determined that the sensor unit 30 has moved. Further, for example, if the measurement surface 24 is stationary, keeping a certain distance from the skin surface 10, so that the levels of the detection signals from the light-receiving parts 34 and 36 are constant, it is determined that the sensor unit 30 has not moved.

Further, if there is no variation in the detection signal waveform of the light-receiving parts 34 and 36 in S20, it is determined that the sensor unit 30 has not moved from the position opposed to the measurement region, and the process proceeds to S21, where it is determined whether the stationary state of the sensor unit 30 has continued for a predetermined time (for example, 30 seconds). If the stationary state of the sensor unit 30 is less than the predetermined time in S21, the above-described process of S20 is repeated. However, if the stationary state of the sensor unit 30 has continued for the predetermined time or more in S21, the measurement process is in the same measurement region, so that the process proceeds to S22 and the measurement process is temporarily suspended to avoid energy consumption of the battery 33 mounted in the blood flow measuring unit 20. In the suspended state of S22, the blood flow measuring part 20 is placed on the charger 56, so that the battery 33 is charged. When the blood flow measuring part 20 is picked up from the charger 56, the process returns again to S11, and the measurement process is resumed.

FIG. 6 is a longitudinal cross-sectional view illustrating a first variation of the blood flow measuring part 20. In FIG. 6, the same parts as those of the first embodiment are given the same characters, and a description thereof is omitted.

As illustrated in FIG. 6, a sensor unit 30A of a blood flow measuring unit 20A of the first variation includes the light-emitting part 32, the paired light-receiving parts 34 and 36, and an optical path splitting member 38.

The optical path splitting member 38 is formed of, for example, a holographic optical element (HOE) using a hologram. The light-emitting part 32 and the paired light-receiving parts 34 and 36 are mounted on the upper surface of the optical path splitting member 38, whose lower surface forms the measurement surface 24. Therefore, when the laser light A from the light-emitting part 32 is emitted onto the skin surface 10 of any measurement region through the optical path splitting member 38, some light components of the laser light A are reflected from the skin surface 10, and the remaining light components are transmitted through a blood flow running through the blood vessel 12 under the skin surface 10 to propagate to the measurement surface 24. Then, each of the paired light-receiving elements 34 and 36 receives light propagated to the optical path splitting member 38, and outputs a detection signal corresponding to the amount of received light (the light intensity of reflected light and transmitted light).

Figure 7A:
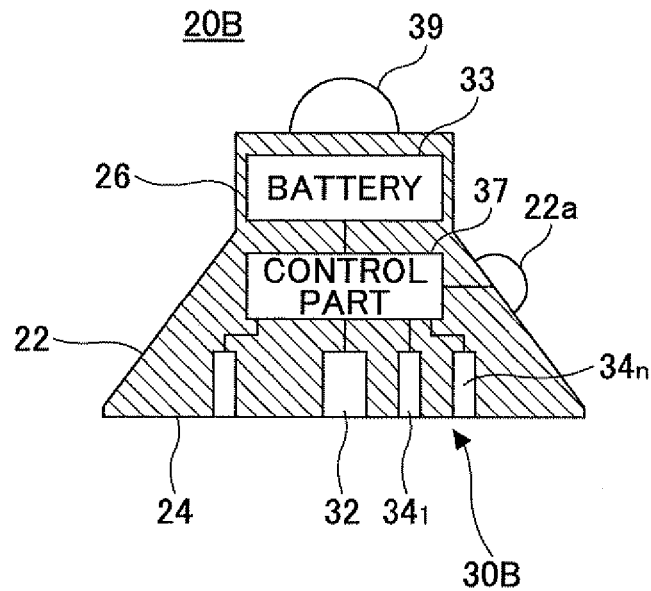
FIG. 7A is a longitudinal cross-sectional view illustrating a second variation of the blood flow measuring part.
Figure 7B:
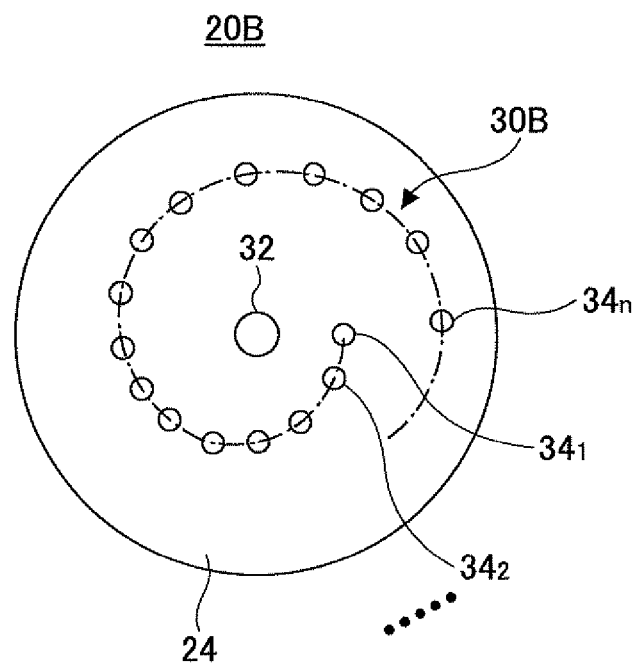
FIG. 7B is a bottom view of the second variation of the blood flow measuring part.

FIG. 7A is a longitudinal cross-sectional view illustrating a second variation of the blood flow measuring part 20. FIG. 7B is a bottom view of the second variation of the blood flow measuring part 20. In FIG. 7A and FIG. 7B, the same parts as those of the first embodiment are given the same characters, and a description thereof is omitted.

As illustrated in FIGS. 7A and 7B, a sensor unit 30B of a blood flow measuring unit 20B of the second variation has the light-emitting part 32 attached to the center (as viewed from below) of the measurement surface 24. Further, multiple light-receiving parts $34_1$ through $34_n$ are spirally arranged around the light-emitting part 32. That is, the multiple light-receiving parts $34_1$ through $34_n$ are circumferentially arranged at predetermined intervals at different radial positions from the light-emitting part 32.

The light emitted onto the skin surface 10 from the light-emitting part 32 is split into light reflected from the skin surface 10 and light transmitted through the skin surface 10 and propagated, so as to be received by the multiple light-receiving parts $34_1$ through $34_n$.

The multiple light-receiving parts $34_1$ through $34_n$ receive the amounts of light corresponding to the distances (radial positions) from the light-receiving part 32, and output detection signals corresponding to the conditions of the displacements of a blood vessel and tissues around the blood vessel. In the second variation, the multiple light-receiving parts $34_1$ through $34_n$ are arranged to surround the light-emitting part 32. Therefore, it is possible to detect light propagation intensity in any direction (any direction in a plane perpendicular to the axis of the light-emitting part 32) from the light-emitting part 32. Therefore, the blood flow measuring unit 20B is not restricted in its moving direction with the measurement surface 24 close and opposed to the skin of a subject, and may be moved in any of the directions in which the multiple light-receiving parts $34_1$ through $34_n$ are arranged.

Second Embodiment

Figure 8:
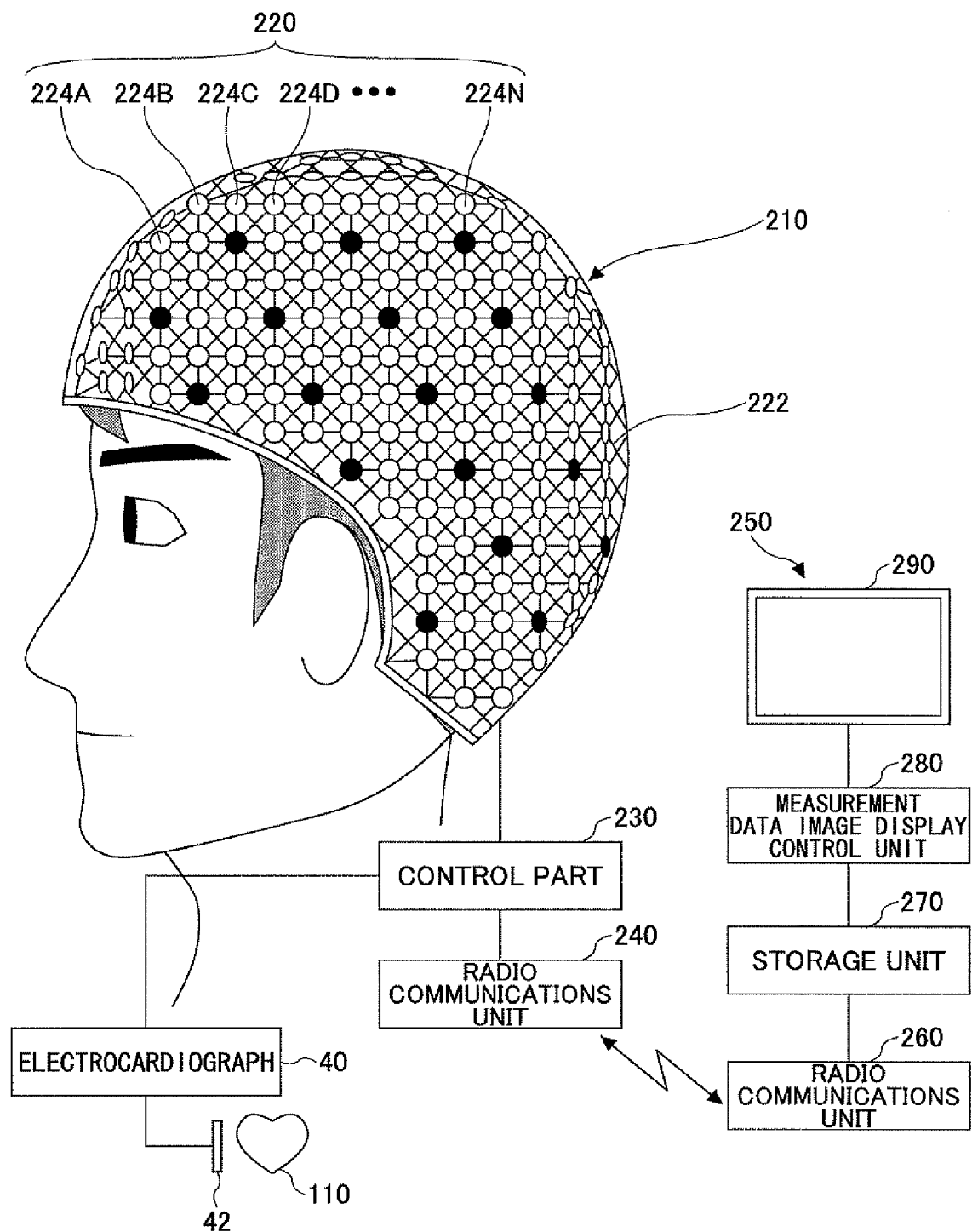
FIG. 8 is a system configuration diagram of a brain blood vessel characteristics measuring system using a second embodiment of the blood vessel characteristics measuring apparatus according to the present invention.

FIG. 8 is a system configuration diagram illustrating a brain blood vessel characteristics measuring system using a second embodiment of the blood vessel characteristics measuring apparatus according to the present invention. As illustrated in FIG. 8, a brain blood vessel characteristics measuring system 200 includes a blood vessel characteristics measuring apparatus 210 and a data management unit 250. The data management unit 250 manages data measured by the blood vessel characteristics measuring apparatus 210. In FIG. 8, only one side of the head part of the blood vessel characteristics measuring apparatus 210 is illustrated, while the other side, which is on the bottom side of the paper plane, has the same configuration.

The blood vessel characteristics measuring apparatus 210 includes a blood flow measuring part 220, a control part 230, and a radio communications unit 240. The blood flow measuring part 220 includes a netted base 222 formed into a hemispheric shape corresponding to a head shape for attachment to a head; and multiple sensor units 224. The sensor units 224 are supported at predetermined intervals by the netted base 222, and output detection signals of the amounts of transmitted light measured at respective measuring points of the head to the control part 230.

The control part 230 derives brain blood vessel characteristics based on the detection signals detected by the sensor units 224, and measures the condition of brain activity (an erythrocyte distribution). Further, the control part 230 contains a control program that executes such computation as to cancel components due to oxygen saturation contained in signals obtained from two or more light-receiving parts.

The radio communications unit 240 transmits measurement results (blood flow data) output from the control part 230 to an external apparatus by radio.

The blood vessel characteristic measuring apparatus 210 has the optical sensor units 224 (224A through 224N) provided on the netted base 222. Therefore, it is possible for the blood vessel characteristic measuring apparatus 210 to measure blood flows throughout the head at the same time.

The sensor units 224 are held through intersecting portions of the netted base 222. Further, the quadrangular linking structures of the netted base 222 are stretchable, deforming into rhombuses in accordance with the surface shape of a head to which the netted base 222 is attached. Therefore, the netted base 222 is allowed to deform into a spherical shape corresponding to the surface shape of the head.

According to the netted base 222, netted arm parts (four to eight) connected to each intersecting portion are formed of an elastic resin material. Therefore, the elasticity of the material allows the measurement surfaces of the multiple sensor units 224 to be close to the surface of the head to which the netted base 222 is attached. Further, the end portions of the multiple sensor units 224 are also allowed to be close (without contact) to the surface of the head, which is an object of measurement.

In this embodiment, the sensor units 224 are approximately 10 mm to approximately 50 mm in diameter. Approximately 150 to approximately 300 sensor units 224 are attached to the hemispheric netted base 222 with a predetermined arrangement pattern (at predetermined intervals). The multiple sensor units 224 are individually managed in advance with address data according to the measurement positions of the object of measurement. The measurement data obtained from the sensor units 224 are transmitted and stored with their respective address data.

It is desirable that the multiple sensor units 224 (224A through 224N) be arranged at regular intervals in a matrix manner as an arrangement pattern. However, the shape of the head, which is an object of measurement, is not uniform, and subjects vary in the size and curved surface shape of the head. Therefore, the multiple sensor units 224 may be disposed at irregular intervals.

Further, the blood vessel characteristics measuring apparatus 210 has the radio communications unit 240 as an output part. Therefore, in this embodiment, the blood vessel characteristics measuring apparatus 210 is used in combination with the data management unit 250, which manages blood flow data transmitted from the radio communications unit 240. Further, the blood vessel characteristics measuring apparatus 210 may also transmit data to other external apparatuses (for example, electronic apparatuses such as a personal computer or apparatuses to be controlled, such as an actuator).

The data management unit 250 includes a radio communications unit 260, a storage unit 270, a measurement data image display control unit 280, and a monitor 290. The radio communications unit 260 receives measurement data transmitted from the radio communications unit 240. The storage unit 270 stores the addresses of light-emitting points obtained from the radio communications unit 260, the addresses of light-receiving parts that have received light, and measurement data including measurement signals (received light signals) according to the amounts of light received. The measurement data image display control unit 280 creates image data based on blood vessel characteristics measurement data (the modulus of elasticity of a blood vessel, the amount of plaque inside a blood vessel, and the degree of arteriosclerosis) corresponding to a pulse wave velocity supplied via the storage unit 270. The monitor 900 displays the image data of measurement results created by the measurement data image display control unit 280.

Further, the data management unit 250 is capable of performing radio communications with the blood vessel characteristics measuring apparatus 210. Therefore, the data management unit 250 may be installed in a location distant from the blood vessel characteristics measuring apparatus 210. For example, the data management unit 250 may be installed in a location out of sight of a subject.

Figure 9:
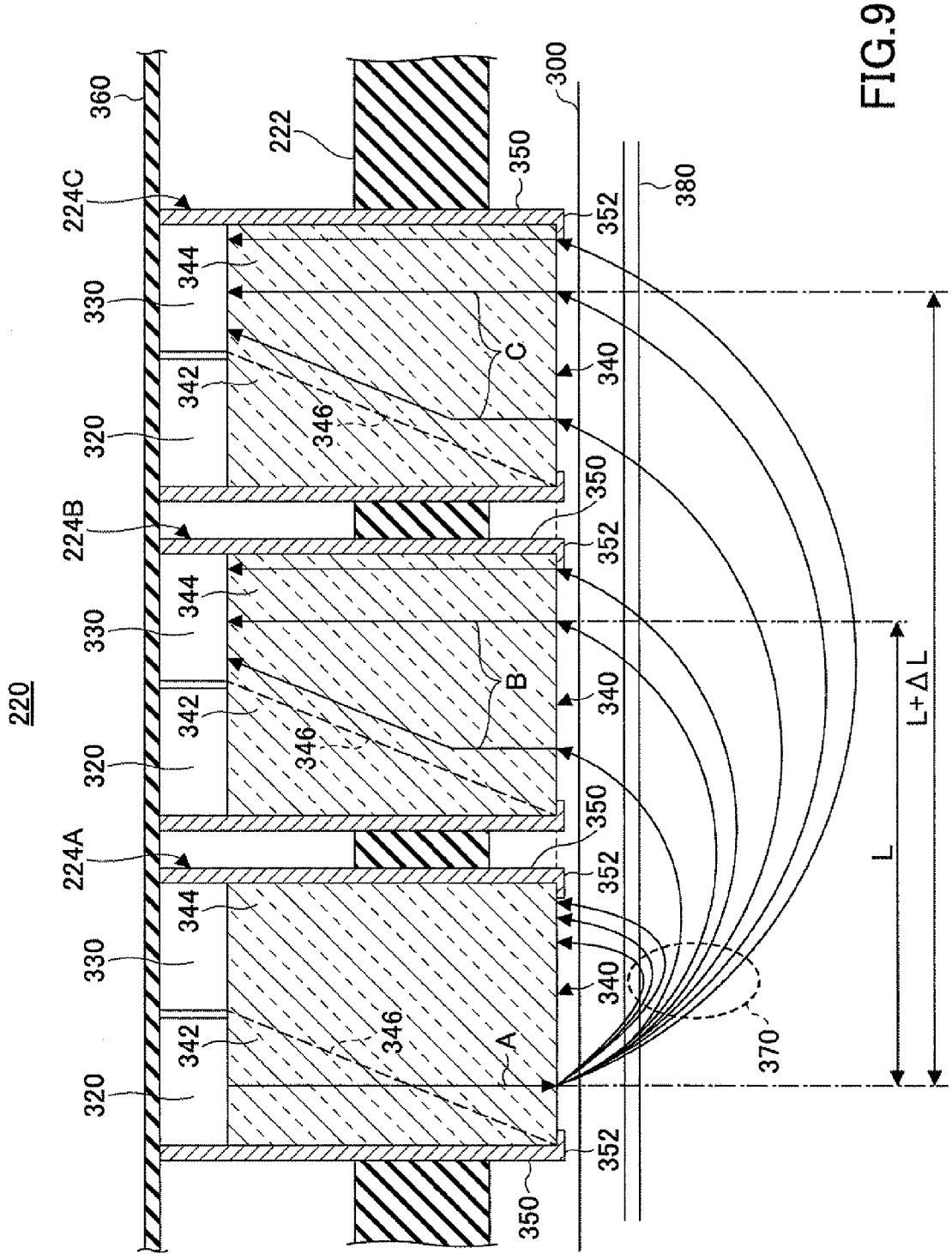
FIG. 9 is a diagram illustrating an attachment structure of sensor units on a larger scale.

FIG. 9 is a diagram illustrating an attachment structure of the sensor units 224 on a larger scale. FIG. 9 illustrates the state of attachment of the sensor units 224A, 224B, and 224C among the multiple sensor units 224 arranged. As illustrated in FIG. 9, the sensor units 224A, 224B, and 224C are fixed to the flexible netted base 222 with an adhesive agent or the like. Accordingly, the sensor units 224A, 224B, and 224C are fixed to corresponding attachment holes of the netted base 222, so that the sensor units 224A, 224B, and 224C are held with their respective end portions in contact with a head surface 300 of a subject. The sensor units 224A, 224B, and 224C have the same configuration, so that the same parts are given the same characters.

The sensor units 224 each include a light-emitting part 320, a light-receiving part 330, and an optical path splitting member 340. The light-emitting part 320, which is formed of a laser diode, emits laser light (emitted light) A onto the head surface 300. The light-receiving part 330 is formed of a light-receiving element that outputs an electrical signal corresponding to the amount of transmitted light received. The optical path splitting member 340 is formed of a holographic optical element (HOE) using a hologram so configured as to have different refractive indexes for the laser light A emitted from the light-emitting part 320 toward a measurement region and entered light B and entered light C that have entered through the measurement region to travel to the light-receiving part 330.

Further, a brain wave measurement electrode 350 for measuring brain waves is fit to the periphery of the optical path splitting member 340. The brain wave measurement electrode 350 is formed to have a cylindrical shape and to extend over the end surface to the side surface of the optical path splitting member 340. The upper end of the brain wave measurement electrode 350 is electrically connected to the interconnection pattern of a flexible wiring board 360.

The light-emitting part 320 and the light-receiving part 330 have their respective upper surfaces mounted on the lower surface of the flexible wiring board 360. An interconnection pattern connected to the control part 230 is formed on the flexible wiring board 360. The connection terminals of the light-emitting part 320 and the light-receiving part 330 are electrically connected by soldering or the like to the interconnection pattern at positions corresponding to the sensor units 224. The flexible wiring board 360 may be flexed in accordance with a head shape when the ends of the sensor units 224 come into contact with the measurement region. Thus, the flexible wiring board 360 is so configured as to prevent occurrence of wire breakage at the time of performing an attachment or detachment operation.

The brain wave measurement electrode 350 includes a contact 352, which is bent inward at the end of the brain wave measurement electrode 350 to project relative to the end face of the optical path splitting member 340. Therefore, when the end face of the optical path splitting member 340 comes into contact with the measurement region, the contact 352 also comes into contact with the measurement region, thus making it possible to measure brain waves. Further, it is also possible to form the brain wave measurement electrode 350 on the periphery and end edge portion of the optical path splitting member 340 by providing a coat of an electrically conductive film by a thin film deposition method such as vapor deposition or plating. Further, it is also possible to form, for example, a transparent electrically conductive film of indium tin oxide, referred to as ITO, as the material of the brain wave measurement electrode 350, on the periphery and end edge portion of the optical path splitting member 340. In the case of forming the brain wave measurement electrode 350 with the transparent electrically conductive film, the brain wave measurement electrode 350 has a light transmitting characteristic. Therefore, it is possible to cover the periphery and entire end face of the optical path splitting member 340 with the brain wave measurement electrode 350.

Further, usually, it is impossible to measure brain waves while measuring the condition of a blood flow by taking a tomogram of a brain, etc. However, by providing the sensor units 224 with the brain wave measurement electrodes 350, it is possible to measure blood flows and brain waves simultaneously, so that it is possible to analyze the correlation between blood flows and brain waves in the brain in detail. In the case of measuring the pulse wave velocity of the brain, the measurement may be performed without the sensor units 224 contacting the head of a subject. In the case of using the sensor units 224 in a contactless manner, the measurement of brain waves with the brain wave measurement electrodes 350 is not performed.

In the case of measuring brain blood vessel characteristics, the control part 230 selects any of the multiple arranged sensor units 224, and causes the light-emitting part 320 of the selected sensor unit 224 to emit the laser light A. At this point, the laser light A emitted from the light-emitting part 320 is output at such a wavelength λ (λ≈805 nm) as is not affected by oxygen saturation.

Further, the sensor units 224 are held with their respective ends (the end faces of the respective optical path splitting member 340) in contact with the measurement region of the head. The laser light A emitted from the light-emitting part 320 is made incident toward the inside of the brain from a direction perpendicular to the scalp of the head through the optical path splitting member 340. Inside the brain, the laser light A travels toward the center of the brain, and the laser light A propagates around the position of incidence as a base point along the surface of the brain. Light propagation paths 370 of the laser light A inside the brain are arc-shaped as viewed from a side, and return to the scalp surface 300 through a blood vessel 380 of the head.

The light that has thus passed through the light propagation paths 370 reaches the sensor units 224B and 224C on the light-receiving side while changing its amount of transmitted light to that according to the amount or concentration of erythrocytes contained in blood flowing through the blood vessel 380. Further, the amount of transmitted light of the laser light A gradually decreases in the process of its propagation through the inside of the brain. Therefore, the light reception levels of the light-receiving parts 330 decrease in proportion to the distance of the laser light A from its position of incidence as a base point. Accordingly, the amount of transmitted light received varies depending on the distance of the laser light A from its position of incidence.

Here, when the blood flow measuring part 220 of the blood vessel characteristics measuring apparatus 210 is attached to the head of a subject to measure the brain blood vessel characteristic of the subject, the following data processing is performed. For example, the degree of arteriosclerosis of the subject is believed to change slowly compared with the speed of scanning light-emitting points. Therefore, light reception data (measurement data) are stored in the database of the storage unit 270 while successively scanning the light-emitting points of the light-emitting parts 320. The detection value (received light intensity) with respect to each measuring point does not differ greatly with a shift in the light-emitting points, and the value T of the phase difference between an electrocardiographic waveform and a pulse wave at each measuring point remains substantially the same no matter which light-emitting point's light is used for the measurement.

Further, according to the blood vessel characteristics measuring apparatus 210, the multiple sensor units 224 are arranged evenly over the entire head, so that when one of the light-emitting parts 320 emits light, it is theoretically possible to read detection signals from all of the light-receiving parts 330. However, in a practical measurement of the blood vessel characteristics of a head, the measurement may be performed effectively if the measurement data (detection signals obtained by receiving light of intensity effective for measurement) of a range of the light-receiving part 330 adjacent to the light-emitting part 320 of the measurement position and the light-receiving part 330 next to that light-receiving part 330 are used. Accordingly, at each of the successive light emissions of the light-emitting parts 320, measurement data (a phase difference or various blood vessel characteristics) based on received light signals (detection signals) from the light-receiving parts 330 of a predetermined range (at least two next to the light-emitting point, or all) are correlated with the measurement position and stored in the database of the storage unit 270 via the radio communications unit 240 and 260. Thereby, the measurement data of the entire head are collected into the database of the storage unit 270 when a single round of scanning of all of the light-emitting parts 320 is completed.

Further, the data management unit 250 totals the values of blood vessel characteristics (for example, the degree of arteriosclerosis) at individual measurement positions successively obtained at the adjacent light-receiving parts 330 within a predetermined range from a light-emitting point while the first (Address 1) light-emitting part 320 through the last (Address N) light-emitting part 320 emit light one after another, and stores the total value in the database of the storage unit 270. Then, the measurement data image display control unit 280 generates a blood vessel characteristic measurement image representing a head arteriosclerosis degree distribution based on the measurement data of the entire head stored in the database of the storage unit 270, and displays the blood vessel characteristic measurement image on the monitor 290.

Further, the data management unit 250 determines the average of the measurement data of each measurement position, and stores the average of each measurement position in the database of the storage unit 270. Then, the measurement data image display control unit 280 may generate a blood vessel characteristic measurement image representing a head arteriosclerosis degree distribution based on the averages of the measurement data, and display the blood vessel characteristic measurement image on the monitor 290.

In FIG. 9, letting the sensor unit 224A located at the left end be a base point on the light-emitting side, the sensor unit 224A itself, the sensor unit 224B to its right, and the sensor unit 224C further to its right are base points on the light-receiving side (measuring points).

The optical path splitting member 340 is so formed as to cause the laser light A to travel straight and guide the entered light B or C to the light receiving part 330 by, for example, changing the density distribution of a transparent acrylic resin. Further, the optical path splitting member 340 includes an emission-side transmission region 342, an entrance-side transmission region 344, and a refraction region 346. The emission-side transmission region 342 transmits the laser light A emitted from the light-emitting part 320 from the base-end side (the upper-surface side in FIG. 9) to the end side (the lower-surface side in FIG. 9). The entrance-side transmission region 344 transmits light propagated through the brain from the end side (the lower-surface side in FIG. 9) to the base-end side (the upper-surface side in FIG. 9). The refraction region 346 is formed between the emission-side transmission region 342 and the entrance-side transmission region 344. The refraction region 344 has a disposition to transmit the laser light A and to reflect light (the entered light B and the entered light C) passing through a blood flow. Further, the refraction region 346 is formed by, for example, changing the density of the acrylic resin or providing a thin metal film or dispersing metal particulates in the region. Thereby, the entire light that has entered the optical path splitting member 340 from its end is gathered at the light-receiving part 330.

Figure 10A:
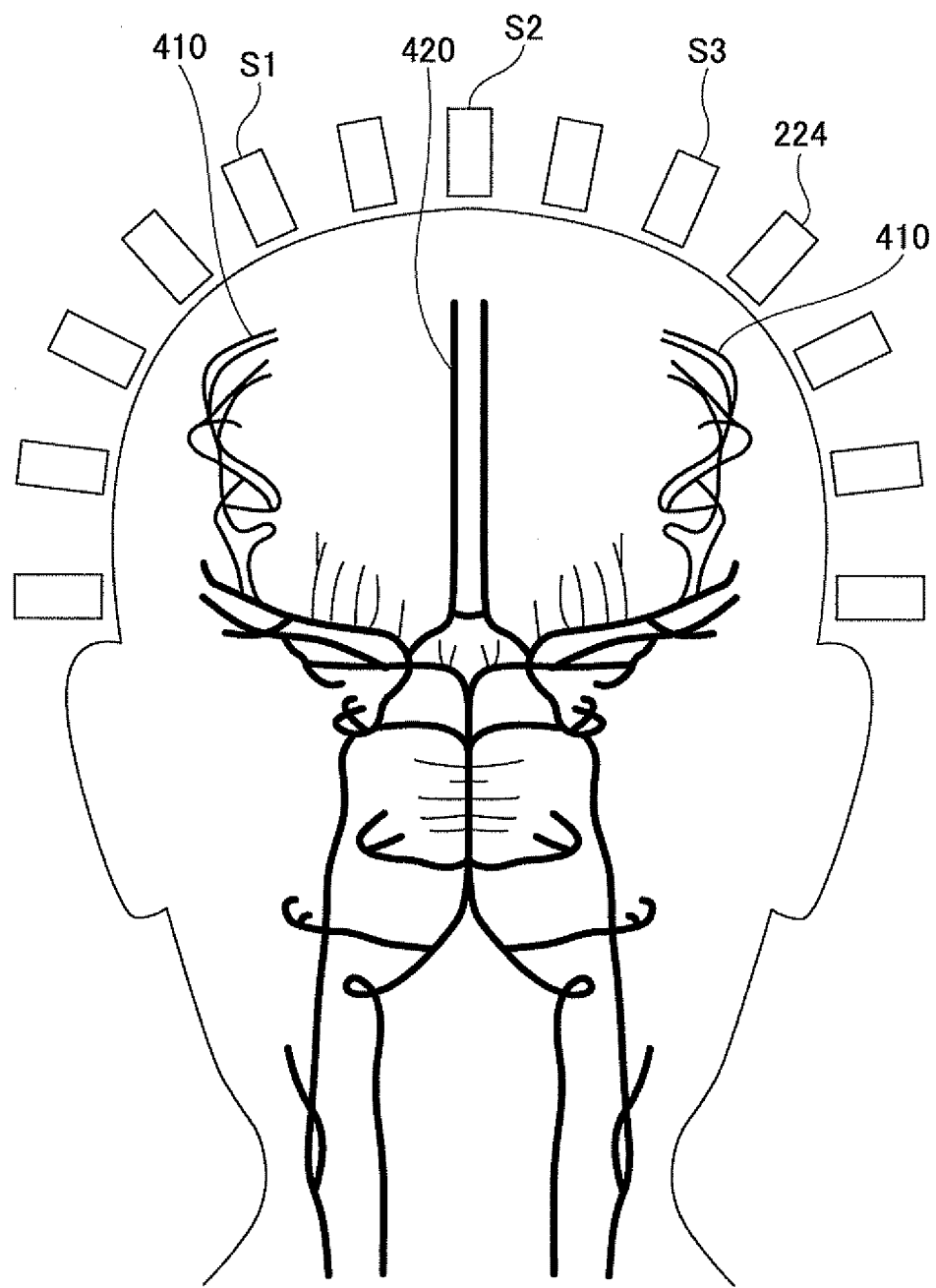
FIG. 10A is a diagram typically illustrating arteries in a rear view of a head.
Figure 10B:
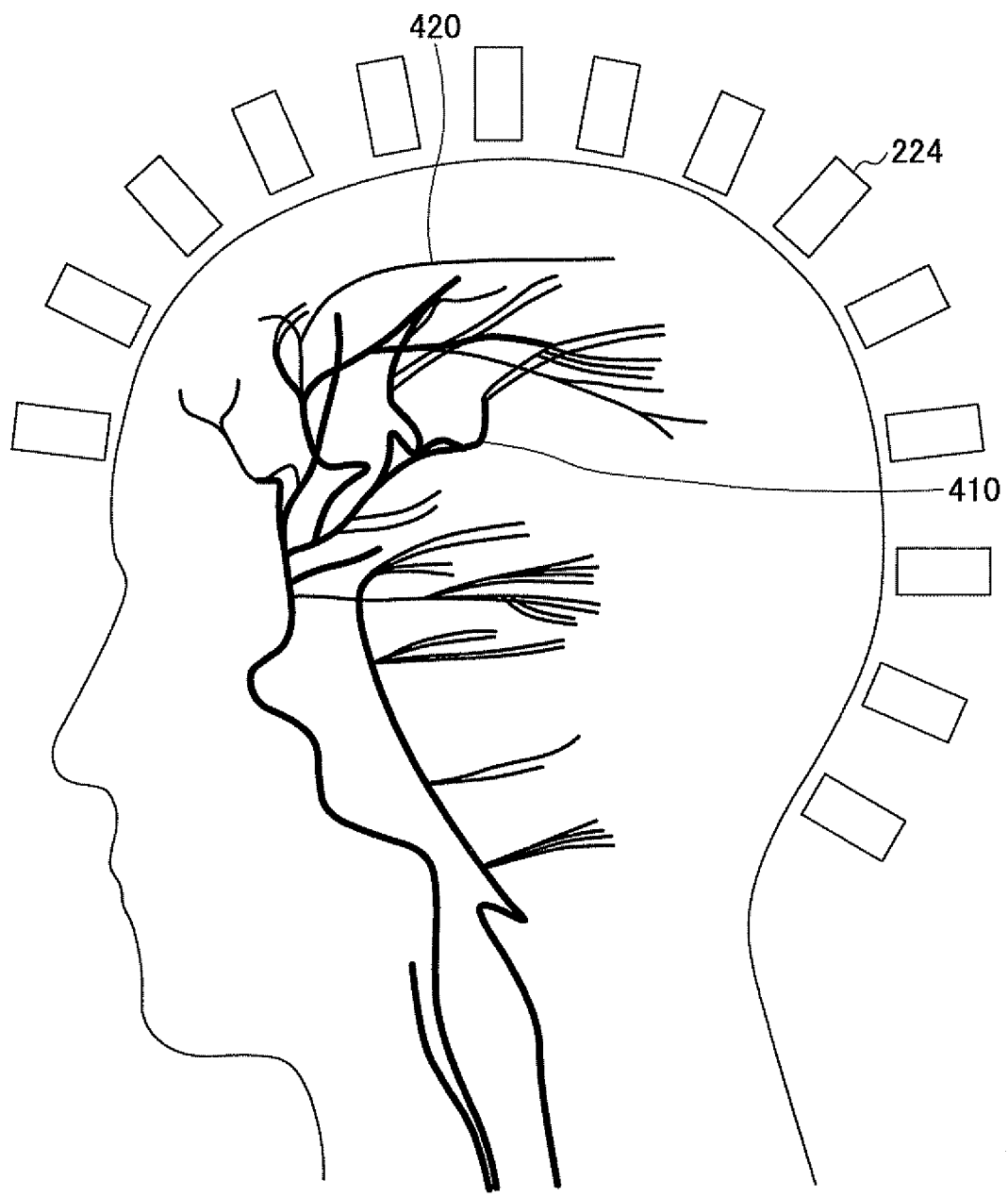
FIG. 10B is a diagram typically illustrating arteries in a left-side view of the head.

Here, a description is given of brain arteries to become a measurement region. FIG. 10A is a diagram typically illustrating arteries in a rear view of a head. FIG. 10B is a diagram typically illustrating arteries in a left-side view of the head. As illustrated in FIG. 10A and FIG. 10B, arteries supplying a brain with blood includes middle cerebral arteries 410 and anterior cerebral arteries 420. Arteries connected to the middle cerebral arteries 410 and the anterior cerebral arteries 420 on their upstream side are not measured in this embodiment. Therefore, a description of arteries other than the middle cerebral arteries 410 and the anterior cerebral arteries 420 is omitted here.

When the blood flow measuring part 220 is attached to the head of a subject, the blood vessel characteristics measuring apparatus 210 is held with the multiple sensor units 224 positioned at respective measuring points of the head with the elasticity of the netted base 222 and each measurement surface opposed to the head surface 300. With the blood flow measuring part 220 attached to the head, the multiple sensor units 224 emit light onto the surface of the brain, and pulse wave velocities in brain arteries are measured from changes in the received amounts of light propagated through the brain, so that the blood vessel characteristics (the modulus of elasticity of a blood vessel, the amount of plaque inside a blood vessel, and the degree of arteriosclerosis) of the middle cerebral arteries 410 and the anterior cerebral arteries 420 may be measured.

Figure 11:
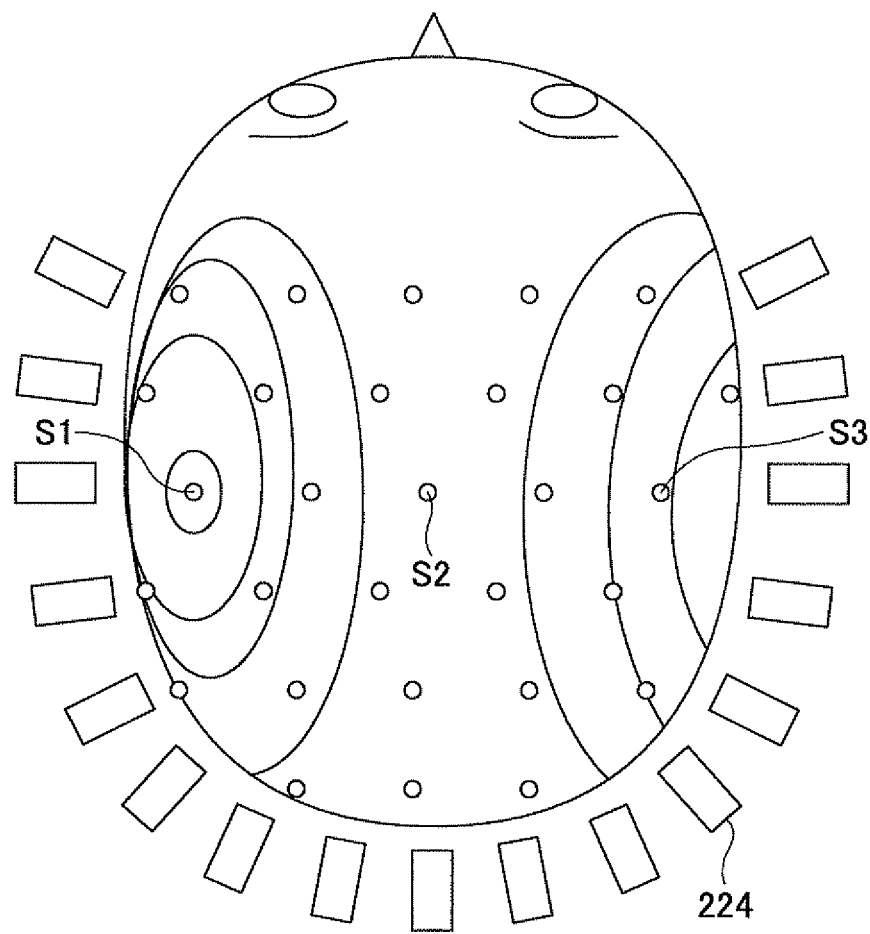
FIG. 11 is a plan view of the head of a subject as viewed from above.

Here, a description is given of the principle of the measurement of the pulse wave velocity of a brain artery. FIG. 11 is a plan view of the head of a subject as viewed from above. As illustrated in FIG. 11 and FIG. 10A, for example, it is assumed that measurement positions where light propagated through the brain at the time of light emission is received are S1, S2, and S3. Pulse wave velocities due to blood flows running through the middle cerebral arteries 410 and the anterior cerebral arteries 420 are detected with the sensor units 224 disposed at the measurement positions S1, S2, and S3. The measurement method employed is to compare a cardiac potential waveform obtained from the electrocardiograph 40 and the waveform of a signal output from each of the sensor units 224 at the measurement positions, determine a pulse wave velocity from the phase difference, and derive blood vessel characteristics corresponding to the pulse wave velocity.

Figure 12:
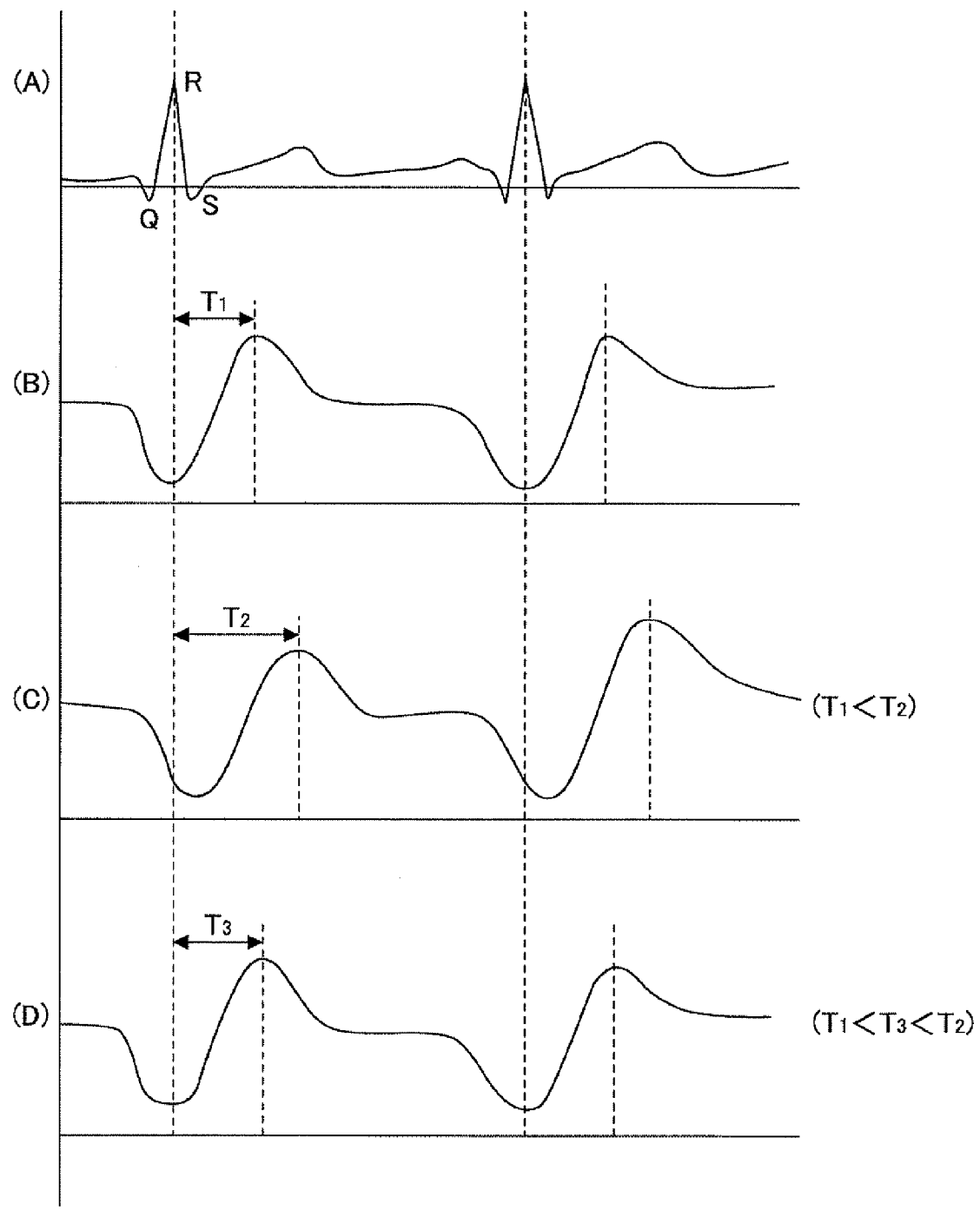
FIG. 12 is a waveform chart illustrating the detection signal waveform of an electrocardiograph and the detection signal waveforms of the sensor units at measurement positions S1, S2, and S3.

FIG. 12 is a waveform chart illustrating the detection signal waveform of the electrocardiograph 40 and the detection signal waveforms of the sensor units 224 at the measurement positions S1, S2, and S3. As illustrated in FIG. 12, the cardiac potential signal waveform (A) detected by the electrocardiograph 40 is compared with the light-receiving part detection signal waveforms (B) through (D), and phase differences T1 through T3 between the peak value of the R wave among the Q wave, R wave, and S wave of the cardiac potential signal waveform (A) and the lowest values of the light-receiving part detection signal waveforms (B) through (D) are determined.

The phase differences T1 through T3 have a relationship of T1<T3<T2, which varies in accordance with the pulse wave velocities. For example, it is assumed that the normal value (threshold) of a phase difference is T0. In this case, if T1<T3<T0 and T0<T2, the pulse wave velocity of the middle cerebral artery 410 of the right brain is lower than the normal value. Thereby, it is possible to determine that blood vessel characteristics are lowered and arteriosclerosis has occurred in the middle cerebral artery 410 of the right brain.

Figure 13:
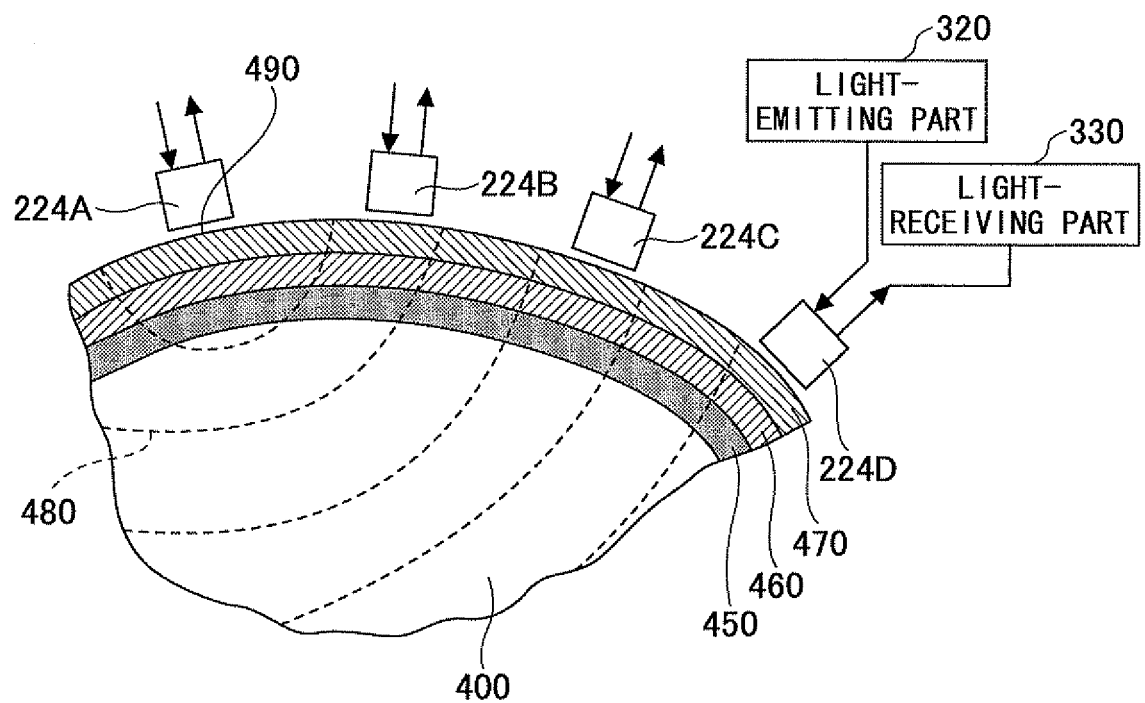
FIG. 13 is a diagram for illustrating a principle in the case of detecting blood vessel characteristics from a blood flow of a brain.

FIG. 13 is a diagram for illustrating a principle in the case of detecting blood vessel characteristics from a blood flow of a brain. As illustrated in FIG. 13, a brain 400 is covered with spinal fluid 450, a skull 460, and a scalp 470. The sensor units 224 of the blood flow measuring part 220 measure blood flows with the end faces of their respective optical path splitting members 340 close and opposed (without contact) to the scalp 470. The laser light A emitted from the light-emitting part 320 of the sensor unit 224A is partly reflected from the scalp 470, but the remaining light is transmitted through the scalp 470, the skull 460, and the spinal fluid 450 to travel into the brain 400. Then, of the light emitted onto the head, the light that has traveled to the brain 400 propagates in radiating directions (a depth direction and radial directions) with an arc pattern 480 as indicated by broken lines in FIG. 13.

With respect to the propagation of light transmitted through the brain 400, as the distance from a base point 490 onto which the laser light A has been emitted increases in radial directions, the light propagation path increases to lower the light transmission characteristic. Therefore, the light reception level (the amount of transmitted light) of the sensor unit 224B, next to the light-emitting-side sensor unit 224A at a predetermined distance therefrom, is detected to be high. Then, the light reception level (the amount of transmitted light) of the sensor unit 224C, provided next to the sensor unit 224B at the predetermined distance therefrom, is detected to be lower than the light reception level of the sensor unit 224B. Further, the light-receiving part of the light-emitting-side sensor unit 224A also receives light from the brain 400. Detection signals according to the intensities of light received by these multiple sensor units 224 are stored in the storage unit 270 as measurement data. Then, the control part 230 compares the waveform of the measurement data of each sensor unit 224 with the waveform of a cardiac potential signal from the electrocardiograph 40, thereby deriving blood vessel characteristics at each measurement position. Further, by mapping these detection results in the measurement data image display control unit 280, graphic data showing an arteriosclerosis distribution corresponding to pulse wave velocities are obtained.

Accordingly, it is possible to measure changes in blood flows running through the middle cerebral arteries 410 and the anterior cerebral arteries 420 with the detection signal waveforms of the sensor units 224 and to detect pulse wave velocities in the brain 400 from the measurement data of the blood flow changes.

Figure 14:
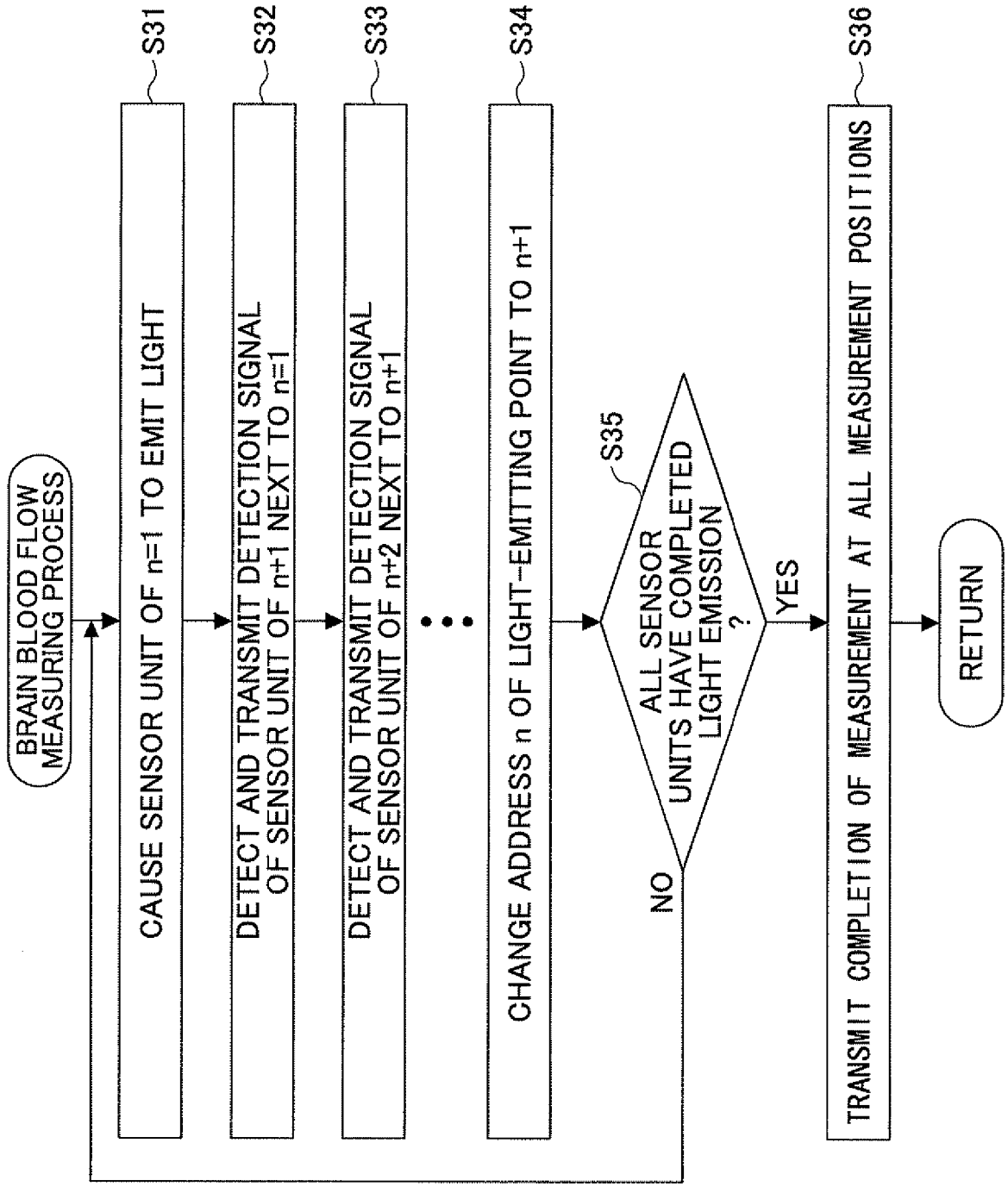
FIG. 14 is a flowchart for illustrating a brain blood flow measuring process executed by a control part of the brain blood vessel characteristics measuring system.

Here, a description is given, with reference to the flowchart of FIG. 14, of a brain blood flow measuring process executed by the control part 230 of the blood vessel characteristics measuring apparatus 210. As illustrated in FIG. 14, first, in S31, the control part 230 selects any sensor unit 224A (a sensor unit of Address Number n=1) from the multiple arranged sensor units, and causes the light-emitting part 320 of the sensor unit 224A to emit laser light onto a measurement region. Next, in S32, the control part 230 causes a detection signal (an electrical signal corresponding to the amount of transmitted light received) output from the light-receiving part 330 of the sensor unit 224B of Address Number n=n+1 next to Address Number n=1 to be transmitted from the radio communications unit 240 to the data management unit 250. In the data management unit 250, the data of n=n+1 obtained from the radio communications unit 260 are stored in the database of the storage unit 270.

Next, in S33, the control part 230 causes a detection signal (an electrical signal corresponding to the amount of transmitted light received) output from the light-receiving part 330 of the sensor unit 224C of Address Number n=n+2 next to Address Number n=n+1 to be transmitted from the radio communications unit 240 to the data management unit 250. In the data management unit 250, the data of n=n+2 obtained from the radio communications unit 260 are stored in the database of the storage unit 270.

Thus, with the sensor unit 224A that has emitted the laser light A being a base point, the detection signals of all of the sensor units 224 disposed around the sensor unit 224A are transmitted to the data management unit 250.

Then, in S34, the address of the sensor unit to serve as a light-emitting point is changed to n+1. Next, in S35, it is determined whether all the sensor units 224 have emitted light. If all the sensor units 224 have not emitted light in S35, the light-emitting part 320 of the n+1 sensor unit 224B is caused to emit the laser light A, and the process of S31 through S35 is repeated.

Further, if all the sensor units 224 have completed light emission in S35, in S36, the data management unit 250 is notified of completion of the brain blood vessel characteristics measuring process with respect to the subject.

Figure 15:
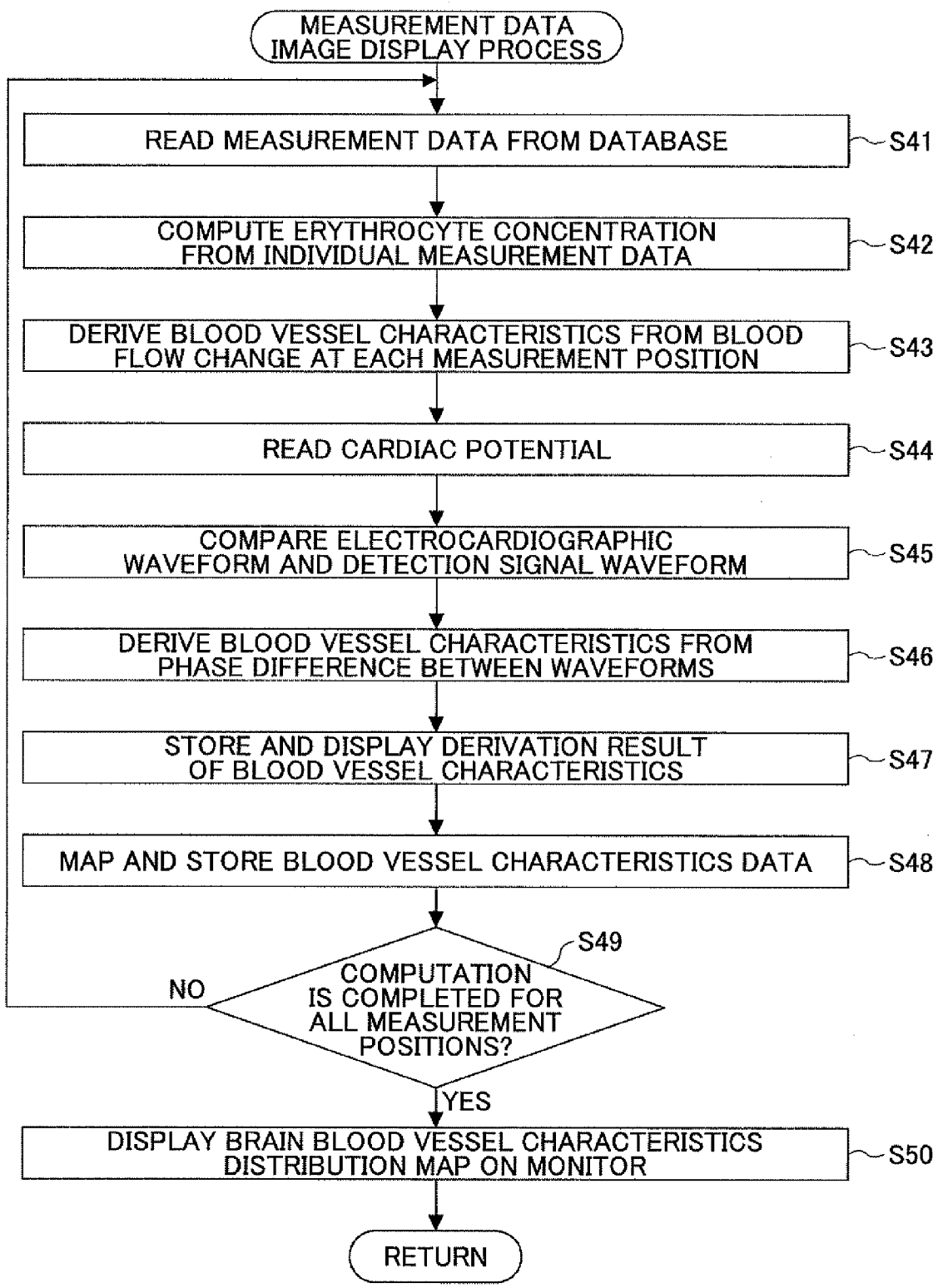
FIG. 15 is a flowchart for illustrating a measurement data image display control process executed by a measurement data image display control unit of a data management unit.

Here, a description is given, with reference to the flowchart of FIG. 15, of a measurement data image display control process executed by the measurement data image display control unit 280 of the data management unit 250. In S41 of FIG. 15, the measurement data image display control unit 280 reads measurement data (data based on the amount of transmitted light according to a blood flow) stored in the database of the storage unit 270. Next, in S42, the erythrocyte concentration Rp or Rpw is computed using the measurement data and Eq. (2) or (3) described above.

Next, in S43, changes in the conditions of the displacements of a blood vessel and tissues around the blood vessel due to a blood flow are determined from a change in the erythrocyte concentration at each measurement position, and blood vessel characteristics at each measurement position are derived based on the conditions of the displacements of the blood vessel and tissues around the blood vessel. That is, the wall displacement data of the blood vessel (the contraction of the inside diameter of the blood vessel) corresponding to the blood flow change are derived from the database.

Next, in S44, a cardiac potential signal detected by the electrocardiograph 40 is read. Then, in S45, the cardiac potential signal waveform of the electrocardiograph 40 and the detection signal waveform (or the waveform of the wall displacement data corresponding to the blood flow change) output from each of the sensor units 224 are compared. In S46, as illustrated in FIG. 12, the phase differences T1 through T3 between the peak value of the R wave among the Q wave, R wave, and S wave of the cardiac potential signal waveform (A) and the lowest values of the light-receiving part detection signal waveforms (B) through (D) are determined.

In S46, the pulse wave velocity is determined by dividing the distance between the heart and the measurement region by the phase difference T between the cardiac potential signal waveform of the electrocardiograph 40 and the detection signal waveform of each of the sensor units 224. Further, the blood vessel characteristics (the modulus of elasticity of the blood vessel, the amount of plaque inside the blood vessel, and the degree of arteriosclerosis) of the measurement region corresponding to the pulse wave velocity are derived from the database of the storage unit 270, so that the degree of arteriosclerosis of the blood vessel in the measurement region is derived. Next, in S47, the degree of arteriosclerosis, which is the result of the derivation of the blood vessel characteristics, is stored in the database of the storage unit 270, and a blood vessel characteristic result image corresponding to the degree of arteriosclerosis obtained this time is displayed on the monitor 290.

Next, in S48, the data on the blood vessel characteristics at the measurement positions are mapped onto the head. Thereby, it is possible to display the presence or absence of arteriosclerosis in brain arteries (such as the middle cerebral arteries 410 and the anterior cerebral arteries 420) as image data on the monitor 290. Then, the head arteriosclerosis data obtained by the mapping are stored in the database of the storage unit 270.

In the above-described mapping, first, the addresses of the sensor units 224 (the light-emitting parts 320 and the light-receiving parts 330) and the corresponding actual measurement position on the head are correlated. Next, the positions (coordinates and depth) of the measurement regions are determined from the addresses of the light-emitting parts 320 and the light-receiving parts 330. Further, the positions of the measurement regions and the measurement data of the measured arteriosclerosis (data on the wall displacement of a blood vessel corresponding to the conditions of the displacements of the blood vessel and tissues around the blood vessel due to a blood flow) are correlated. In defining where in the head the sensor units 224 are actually arranged, rough positions may be preset based on to which positions in the netted base 222 the sensor units 224 are attached. Further, in order to determine the positions in more detail, the head to which the blood flow measuring part 220 is attached may be subjected to imaging from various angles (such as a front direction, a rear direction, lateral directions, and an upward direction) and the addresses of the sensor units 224 may be mapped onto images in correlating the addresses of the sensor units 224 with the actual positions of the head. Further, by causing an image to be displayed with the measurement results superposed on the image, the blood flow condition or the degree of arteriosclerosis of the head of a subject may be, for example, identified by color when displayed. Therefore, it is possible to easily find part of the head of the subject where the condition of a blood flow is considerably poor.

Next, in S49, it is determined whether the detection of blood vessel characteristics by the sensor unit 224 is completed with respect to all measurement positions. If the detection of blood vessel characteristics by the sensor unit 224 is not completed with respect to all measurement positions in S49, the process returns to S41, and the process is repeated from S41.

Further, if the detection of blood vessel characteristics by the sensor unit 224 is completed with respect to all measurement positions in S49, in step S50, an image representing a brain blood vessel characteristics condition showing a distribution of the blood vessel characteristics of the entire head (identifying the presence or absence of arteriosclerosis in the brain of a subject by color) is generated, and a brain blood vessel characteristics distribution map is displayed on the monitor 290.

Thus, an image representing the brain blood vessel characteristics condition of the entire head obtained from blood vessel characteristics data according to the pulse wave velocity measured by the blood vessel characteristics measuring apparatus 210 is displayed on the monitor 290. Therefore, it is possible to understand the blood vessel characteristics condition of a subject with accuracy.

The present international application claims priority based on Japanese Patent Application No. 2008-181471, filed on Jul. 11, 2008, the entire contents of which are incorporated herein by reference.

DESCRIPTION OF THE REFERENCE NUMERALS 10 skin surface
20, 20A, 20B blood flow measuring unit
220 blood flow measuring part
24 measurement surface
26 holding part
30, 30A, 30B sensor unit
32 light-emitting part
33 battery
34 ($34_1$ through $34_n$), 36 light-receiving part
37 control part
38 optical path splitting member
39 radio communications unit
40 electrocardiograph (electrocardiographic measurement part)
42 electrode
50 controller
52 storage unit
54 radio communications unit
60 blood flow measuring part
70 blood vessel displacement deriving part
80 blood vessel condition deriving part
90 monitor
92 measurement image
94 blood vessel characteristic result image
100, 210 blood vessel characteristics measuring apparatus
200 brain blood vessel characteristics measuring system
222 netted base
224 (224A through 224N) sensor unit
230 control part
240, 260 radio communications unit
250 data management unit
270 storage unit
280 measurement data image display control unit
290 monitor
300 head surface
320 light-emitting part 330 light-receiving part
340 optical path splitting member
342 emission-side transmission region
350 brain wave measurement electrode
360 flexible wiring board
370 light propagation path
380 blood vessel
400 brain
410 middle cerebral artery
420 anterior cerebral artery
490 base point

The invention claimed is:

1. A blood vessel characteristics measuring apparatus, comprising:
a sensor unit provided at a position opposed to a measurement region of a subject, the sensor unit including a light-emitting part configured to emit light onto the measurement region, a light-receiving part configured to contactlessly receive the light propagated through the measurement region and output a detection signal corresponding to a light intensity of the received light, and a radio communication part configured to convert the detection signal into a radio signal and transmit the radio signal; and
a controller configured to receive the radio signal transmitted from the radio communication part of the sensor unit, the controller including
a blood flow measuring part configured to measure a displacement of a blood vessel and a displacement of a tissue around the blood vessel caused by a blood flow in the measurement region based on the light intensity read from the received radio signal;
a blood vessel displacement deriving part configured to derive a displacement of a wall of the blood vessel based on the displacement of the blood vessel and the displacement of the tissue around the blood vessel measured by the blood flow measuring part;
an electrocardiographic measurement part configured to measure an electrocardiographic signal of the subject;
a blood vessel condition deriving part configured to determine a pulse wave velocity using a difference between a waveform of the electrocardiographic signal and one of a detection signal waveform obtained from the light-receiving part and a waveform of the derived displacement of the wall of the blood vessel, and to derive a condition of the wall of the blood vessel at each of measurement positions by deriving blood vessel characteristics corresponding to the determined pulse wave velocity from a database, wherein the derived condition of the wall of the blood vessel is a degree of arteriosclerosis, and the derived blood vessel characteristics include a modulus of elasticity of the blood vessel, an amount of plaque inside the blood vessel, and the degree of arteriosclerosis; and
a control part configured to generate a first image based on the measured displacement of the blood vessel and the measured displacement of the tissue around the blood vessel and a second image based on the derived condition of the wall of the blood vessel, and display the first image and the second image on a display.

2. The blood vessel characteristics measuring apparatus as claimed in claim 1, wherein the blood vessel condition deriving part is configured to derive the condition of the wall of the blood vessel at each of the measurement positions based on a phase difference between the waveform of the electrocardiographic signal and the detection signal waveform obtained from the light-receiving part.

3. The blood vessel characteristics measuring apparatus as claimed in claim 1, wherein the blood flow measuring part is configured to optically measure a blood cell component according to the condition of the wall of the blood vessel.

4. The blood vessel characteristics measuring apparatus as claimed in claim 1, wherein:
the sensor unit includes plural of the light-emitting parts configured to emit light onto a plurality of measuring points of the subject and plural of the light-receiving parts configured to contactlessly receive the light propagated through the measuring points, and
the blood vessel condition deriving part is configured to derive the condition of the wall of the blood vessel at each of the measurement positions based on differences between the waveform of the electrocardiographic signal and the detection signal waveform obtained from the light-receiving parts.

5. The blood vessel characteristics measuring apparatus as claimed in claim 4, wherein the light-receiving parts include a first light-receiving part configured to measure a propagation intensity of the light over an upstream portion of the blood vessel in the measurement region; and a second light-receiving part provided on a downstream side of the first light-receiving part over the blood vessel and configured to measure the propagation intensity of the light over a downstream portion of the blood vessel in the measurement region.

6. The blood vessel characteristics measuring apparatus as claimed in claim 1, wherein the sensor unit includes plural of the light-receiving parts configured to contactlessly receive the light propagated through the measurement region and the light-receiving parts are circumferentially arranged at predetermined intervals at different radial positions around the light-emitting part.

7. The blood vessel characteristics measuring apparatus as claimed in claim 1, wherein the sensor unit is provided in a movable blood vessel measuring unit and configured to measure a propagation intensity of the light in any measurement region.

8. The blood vessel characteristics measuring apparatus as claimed in claim 7, wherein the blood flow measuring unit includes:
a battery configured to supply the sensor unit with an electric current.

9. The blood vessel characteristics measuring apparatus as claimed in claim 1, wherein plural of the sensor units are supported at a plurality of points of a netted base configured to be attached to a head of the subject and are configured to measure a propagation intensity of the light at the respective measurement positions of the head of the subject.

10. The blood vessel characteristics measuring apparatus as claimed in claim 9, wherein the blood vessel condition deriving part is configured to derive the condition of the blood vessel at each of the measurement positions of the head based on differences between the waveform of the electrocardiographic signal and detection signal waveforms obtained from the sensor units.

11. The blood vessel characteristics measuring apparatus as claimed in claim 9, wherein:
the blood flow measuring part is configured to map measurement data obtained from the light-emitting parts based on addresses relative to the head, and to store the displacement of the blood vessel in the database with respect to each of the measurement positions corresponding to the addresses, and the blood vessel condition deriving part is configured to generate an image of blood vessel characteristics of the entire head by deriving the condition of the blood vessel at each of the measurement positions of the head by reading the displacement of the blood vessel at each of the measurement positions from the database and extracting the displacement of the blood vessel corresponding to each of the addresses.

12. A blood vessel characteristics measuring method, comprising:

causing a light-emitting part of a sensor unit provided to be opposed to a measurement region of a subject to emit light onto the measurement region, receiving the light propagated through the measurement region and outputting a detection signal corresponding to a light intensity of the received light by a light-receiving part of the sensor unit;

converting the detection signal into a radio signal and transmitting the radio signal by the sensor unit;

receiving the radio signal transmitted from the sensor unit by a controller;

measuring, by the controller, a displacement of a blood vessel and a displacement of a tissue around the blood vessel caused by a blood flow in the measurement region based on the light intensity read from the received radio signal;

deriving, by the controller, a displacement of a wall of the blood vessel based on the measured displacement of the blood vessel and the measured displacement of the tissue around the blood vessel;

measuring, by the controller, an electrocardiographic signal of the subject;

determining, by the controller, a pulse wave velocity using a difference between a waveform of the electrocardiographic signal and one of a detection signal waveform obtained from the light-receiving part and a waveform of the derived displacement of the wall of the blood vessel, and deriving, by the controller, a condition of the wall of the blood vessel at each of measurement positions by deriving blood vessel characteristics corresponding to the determined pulse wave velocity from a database, wherein the derived condition of the wall of the blood vessel is a degree of arteriosclerosis, and the derived blood vessel characteristics include a modulus of elasticity of the blood vessel, an amount of plaque inside the blood vessel, and the degree of arteriosclerosis; and generating, by the controller, a first image based on the measured displacement of the blood vessel and the measured displacement of the tissue around the blood vessel and a second image based on the derived condition of the wall of the blood vessel, and displaying the first image and the second image on a display.

* * * * *